US010267736B2

(12) United States Patent
Lo et al.

(10) Patent No.: US 10,267,736 B2
(45) Date of Patent: Apr. 23, 2019

(54) IMAGING FLOW CYTOMETER USING SPATIAL-TEMPORAL TRANSFORMATION

(71) Applicant: THE REGENTS OF THE UNIVERSITY OF CALIFORNIA, Oakland, CA (US)

(72) Inventors: Yu-Hwa Lo, San Diego, CA (US); Yuanyuan Han, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 201 days.

(21) Appl. No.: 15/514,930

(22) PCT Filed: Sep. 30, 2015

(86) PCT No.: PCT/US2015/053368
§ 371 (c)(1),
(2) Date: Mar. 28, 2017

(87) PCT Pub. No.: WO2016/054293
PCT Pub. Date: Apr. 7, 2016

(65) Prior Publication Data
US 2017/0227466 A1 Aug. 10, 2017

Related U.S. Application Data

(60) Provisional application No. 62/057,799, filed on Sep. 30, 2014.

(51) Int. Cl.
G01N 21/64 (2006.01)
G01N 21/53 (2006.01)
(Continued)

(52) U.S. Cl.
CPC ....... G01N 21/6486 (2013.01); G01N 15/147 (2013.01); G01N 15/1434 (2013.01);
(Continued)

(58) Field of Classification Search
CPC .......... G01N 21/6486; G01N 15/1459; G01N 21/51; G01N 21/53; G01N 15/1434;
(Continued)

(56) References Cited

U.S. PATENT DOCUMENTS 9,217,160 B2 12/2015 O'Shea et al.
2003/0142289 A1 7/2003 Ortyn et al.
(Continued)

FOREIGN PATENT DOCUMENTS

EP 2085797 A2 8/2009

OTHER PUBLICATIONS

Alaynick, et al., "SnapShot: Spinal Cord Development", Cell 146, 2011, pp. 178-178 e171.
(Continued)

Primary Examiner — Hina F Ayub
Assistant Examiner — Amanda Merlino
(74) Attorney, Agent, or Firm — Perkins Coie LLP

(57) ABSTRACT

Methods, systems, and devices are disclosed for imaging particles and/or cells using flow cytometry. In one aspect, a method includes transmitting a light beam at a fluidic channel carrying a fluid sample containing particles; optically encoding scattered or fluorescently-emitted light at a spatial optical filter, the spatial optical filter including a surface having a plurality of apertures arranged in a pattern along a transverse direction opposite to particle flow and a longitudinal direction parallel to particle flow, such that different portions of a particle flowing over the pattern of the apertures pass different apertures at different times and scatter the light beam or emit fluorescent light at locations associated with the apertures; and producing image data associated with the particle flowing through the fluidic
(Continued)

channel based on the encoded optical signal, in which the produced image data includes information of a physical characteristic of the particle.

26 Claims, 14 Drawing Sheets

(51) Int. Cl.
  *G01N 21/51* (2006.01)
  *G01N 15/14* (2006.01)
  *G01F 17/00* (2006.01)
  *G01N 15/10* (2006.01)
  *G02B 21/00* (2006.01)

(52) U.S. Cl.
  CPC ......... *G01N 15/1459* (2013.01); *G01N 21/51* (2013.01); *G01N 21/53* (2013.01); *G01F 17/00* (2013.01); *G01N 2015/1006* (2013.01); *G01N 2015/144* (2013.01); *G01N 2015/145* (2013.01); *G01N 2015/1447* (2013.01); *G01N 2201/06113* (2013.01); *G02B 21/002* (2013.01)

(58) Field of Classification Search
  CPC ....... G01N 15/147; G01N 2201/06113; G01N 2015/144; G01N 2015/1006
  See application file for complete search history.

(56) References Cited

U.S. PATENT DOCUMENTS

| | | |
|---|---|---|
| 2011/0090500 A1 | 4/2011 | Hu et al. |
| 2012/0078531 A1 | 3/2012 | Lo et al. |
| 2013/0016335 A1 | 1/2013 | Lo et al. |
| 2013/0083315 A1* | 4/2013 | Lo .................... G01J 3/46 356/73 |
| 2014/0234865 A1 | 8/2014 | Gabriel |

OTHER PUBLICATIONS

Babbe, H. et al., "Clonal expansions of CD8(+) T cells dominate the T cell infiltrate in active multiple sclerosis lesions as shown by micromanipulation and single cell polymerase chain reaction", J Exp Med 192, 2000, pp. 393-404.
Barteneva, et al., "Imaging flow cytometry: coping with heterogeneity in biological systems", J Histochem Cytochem, 2012, 60, pp. 723-733.
Basiji, et al., "Cellular image analysis and imaging by flow cytometry", Clin Lab Med, 2007, 27, pp. 65-viii.
Berdichevsky, Y. et al., "UV/ozone modification of poly(dimethylsiloxane) microfluidic channels", Sensors and Actuators B: Chemical 97, 2004, pp. 402-408.
Bonner, et al., "Fluorescence activated cell sorting", Rev Sci Instrum, 1972, 43, pp. 404-409.
Chen et al., "Specific sorting of single bacterial cells with microfabricated fluorescence-activated cell sorting and tyramide signal amplification fluorescence in situ hybridization", Anal Chem 83, 2011, pp. 7269-7275.
Chen et al., "Microfluidic cell sorter with integrated piezoelectric actuator", Biomed Microdevices 11, 2009, pp. 1223-1231.
Chen et al., "High-Throughput Cell Sorter with Piezoelectric Actuation", Micro Total Anal Syst., 2008, pp. 155-157.
Chen et al., "Scattering-Based Cytometric Detection Using Integrated Arrayed Waveguides With Microfluidics", IEEE Photonics Technology Letters 19, 2007, pp. 441-443.
Chen et al., "High-sensitivity scattering-based detection under symmetrical arrayed-waveguide platform", Digest of the LEOS Summer Topical Meetings, 2006, pp. 52-53.
Chiu et al., "Universally applicable three-dimensional hydrodynamic microfluidic flow focusing", Lab Chip 13, 2013, pp. 1803-1809.
Cho, et al., "Optofluidic flow cytometer employing color-space-time (COST) coding: On-chip multiple fluorescence differentiation", CYTO 2013, San Diego.
Cho et al., "Review Article: Recent advancements in optofluidic flow cytometer", Biomicrofluidics 4, 2010, p. 043001.
Cho, et al., "Human mammalian cell sorting using a highly integrated micro-fabricated fluorescence-activated cell sorter (µFACS)", Lab Chip 10: 2010, pp. 1567-1573.
Cho et al., "Lab-on-a-chip flow cytometer employing color-space-time coding", Appl Phys Lett 97, 2010, p. 093704.
Cho et al., "Optofluidic Waveguides in Teflon AF-Coated PDMS Microfluidic Channels" IEEE Photonics Technol Lett 21, 2009, pp. 1057-1059.
Cho et al., "Microfluidic Photonic Integrated Circuits", Optoelectron Mater Devices 7135, 2008, p. 71350M.
Cho et al., "Micro-fabricated fluorescence-activated cell sorter", Conf Proc IEEE Eng Med Biol Soc 2009, pp. 1075-1078.
Cho et al., "Optofluidic biosensors: miniaturized multi-color flow cytometer and fluorescence-activated cell sorter (microFACS)", Proceedings of SPIE, 2011, San Diego, CA.
Davey et al., "Flow cytometry and cell sorting of heterogeneous microbial populations: the importance of single-cell analyses", Microbiol Rev 60, 1996, pp. 641-696.
Godin et al., "Two-parameter angular light scatter collection for microfluidic flow cytometry by unique waveguide structures", Biomed Opt Express, 2010, 1, pp. 1472-1479.
Godin et al., "On-chip optics for manipulating light in polymer chips", Optoelectron Commun Conf. 2009.
Godin et al., "Microfluidics and photonics for Bio-System-on-a-Chip: a review of advancements in technology towards a microfluidic flow cytometry chip", J Biophotonics 1, 2008, pp. 355-376.
Gorthi et al., "Flourescence imaging of flowing cells using a temporally coded excitation", Optics Express, 2013, vol. 21, p. 5164.
Han et al., "Imaging Cells in Flow Cytometer Using Spatial-Temporal Transformation", Scientific Reports, 2015, 10 pages.
Han et al., "Review: imaging technologies for flow cytometry", Lap Chip, 2016, 16, pp. 4369-4647.
Hanahan et al., "The Hallmarks of Cancer", Cell 100, 2000, pp. 57-70.
Iida et al., "Stem and Progenitor Cell Subsets Are Affected by JAK2 Signaling and Can Be Monitored by Flow cytometry", PLoS One 9, 2014, p. e93643.
Kachel et al., "Fast Imaging in Flow: A Means of Combining Flow-Cytometry and Image Analysis", The Journal of Histochemistry and Cytochemistry, 1979, vol. 27, pp. 335-341.
Lien et al., "High-sensitivity cytometric detection using fluidic-photonic integrated circuits with array waveguides", IIEE Journal of Selected Topics in Quantum Electronics, 11, 2005, pp. 827-834.
Lien et al., "Fluidic photonic integrated circuit for in-line detection", Applied Physics Letters 87, 2005, pp. 194106-194103.
Ma et al., "Brush biopsy with DNA-image cytometry: a useful and noninvasive method for monitoring malignant transformation of potentially malignant oral disorders", Eur Arch Otorhinolaryngol, 2014, 271, pp. 3291-3295.
Marchiani et al., "Characterization and sorting of flow cytometric populations in human semen", Andrology, 2014, 2, pp. 394-401.
Mcconnell et al., "Mosaic copy number variation in human neurons", Science 342, 2013, pp. 632-637.
Meade et al., "Microfluidic flow cytometry: Advancements toward compact, integrated systems", Advanced Optical Flow Cytometry: Methods and Disease Diagnoses, Wiley-VCH Verlag Gmbh & Co. KGaA, 2011, pp. 273-310.
Mei et al., "Counting leukocytes from whole blood using a lab-on-a-chip Coulter counter", Conf Proc IEEE Eng Med Biol Soc 2012, pp. 6277-6280.
Mei et al., "Applying an optical space-time coding method to enhance light scattering signals in microfluidic devices", Biomicrofluidics 5, 2011, p. 034116.

(56) References Cited

OTHER PUBLICATIONS

Meng et al., "Automated quantification of DNA aneuploidy by image cytometry as an adjunct for the cytologic diagnosis of malignant effusion", Anal Cell Pathol (Amst) 36, 2013, pp. 107-115.

Nakazono et al., "Laser-capture microdissection, a tool for the global analysis of gene expression in specific plant cell types: identification of genes expressed differentially in epidermal cells or vascular tissues of maize", Plant Cell 15, 2003, pp. 583-596.

Navin et al., "Tumour evolution inferred by single-cell sequencing", Nature 472, 2011, pp. 90-94.

Oemar et al., "Reduced endothelial nitric oxide synthase expression and production in human atherosclerosis", Circulation 97, 1998, pp. 2494-2498.

Ornstein et al., "Proteomic analysis of laser capture microdissected human prostate cancer and in vitro prostate cell lines", Electrophoresis 21, 2000, pp. 2235-2242.

Prince et al., "Identification of a subpopulation of cells with cancer stem cell properties in head and neck squamous cell carcinoma", PNAS 104, 2007, pp. 973-978.

Schulz et al., "The effect of the DNA conformation on the rate of NtrC activated transcription of *Escherichia coli* RNA polymerase sigma(54) holoenzyme", J Mol Biol 300, 2000, pp. 709-725.

Shapiro et al., "Single-cell sequencing-based technologies will revolutionize whole-organism science", Nat Rev Genet 14, 2013, pp. 618-630.

Varecha t al., "Bioinformatic and image analyses of the cellular localization of the apoptotic proteins endonuclease G, AIF, and AMID during apoptosis in human cells", Apoptosis 12, 2007, pp. 1155-1171.

Wu et al., "Optofluidic device for label-free cell classification from whole blood", Lab Chip, 2012, 12(19), pp. 3791-3797.

Wu et al., "An optical-coding method to measure particle distribution in microfluidic devices", AIP advances 1, 2011, p. 022155.

Zuba-Surma et al., "The ImageStream System: a key step to a new era in imaging", Folia Histochem Cytobiol 45, 2007, pp. 279-290.

Zuba-Surma et al., "Analytical capabilities of the ImageStream cytometer", Methods Cell Biol 102, 2011, pp. 207-230.

Extended European Search Report for European Patent Application No. 15847776.0, dated Jun. 14, 2018, 9 pages.

PCTUS2015/053368, International Search Report and Written Opinion, dated Dec. 28, 2015, 11 pages.

Office Action for Chinese Patent Application No. 201580064914.7, dated Mar. 5, 2019, 8 pages.

* cited by examiner

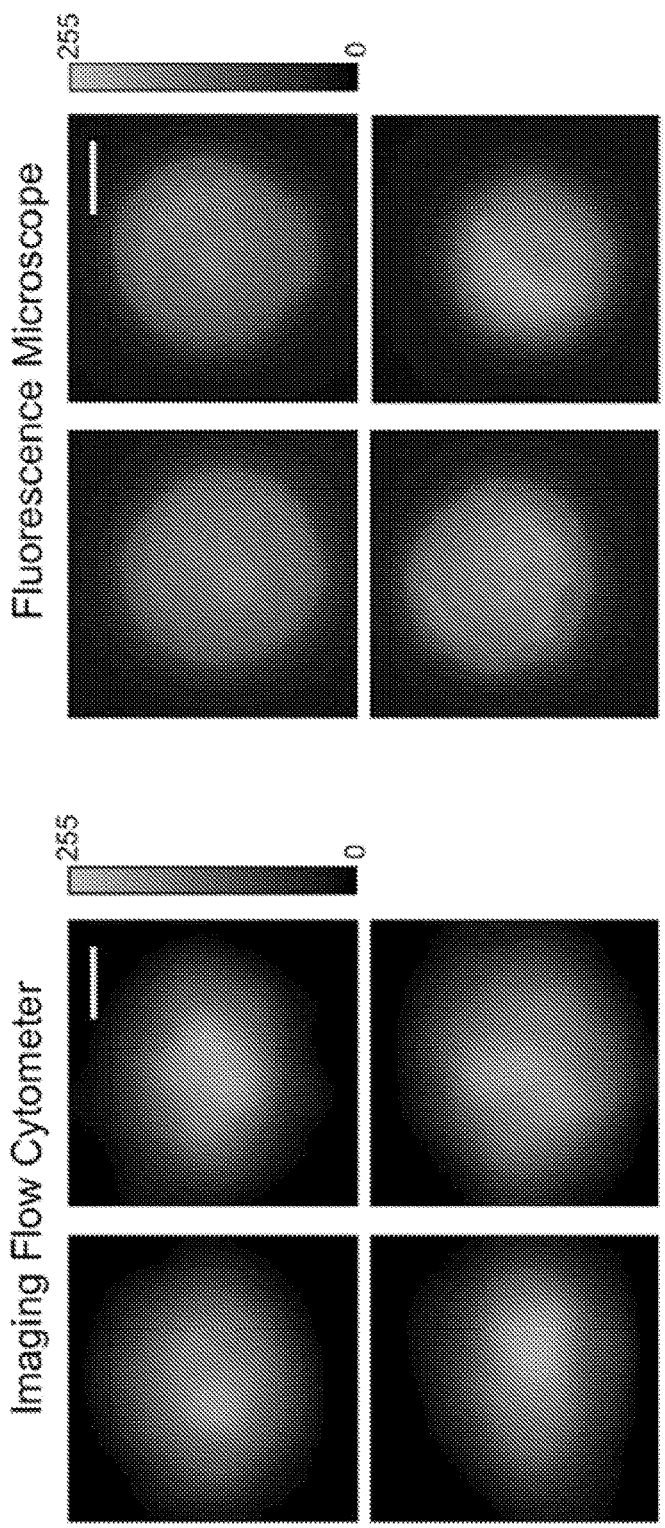

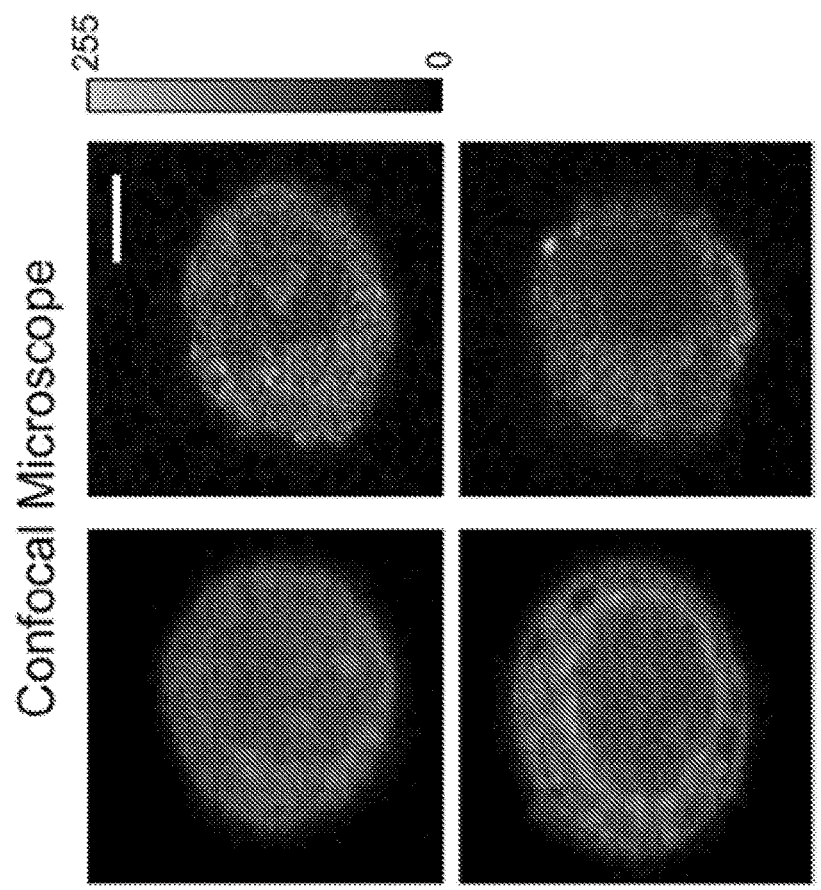

IMAGING FLOW CYTOMETER USING SPATIAL-TEMPORAL TRANSFORMATION

CROSS-REFERENCE TO RELATED APPLICATIONS

This patent document is a 35 USC § 371 National Stage application of International Application No. PCT/US2015/053368, entitled "IMAGING FLOW CYTOMETER USING SPATIAL-TEMPORAL TRANSFORMATION," filed on Sep. 30, 2015, which claims the benefits and priority of U.S. Provisional Patent Application No. 62/057,799, entitled "IMAGING FLOW CYTOMETER USING SPATIAL-TEMPORAL TRANSFORMATION," filed on Sep. 30, 2014. The entire content of the aforementioned patent applications are incorporated by reference as part of the disclosure of this application.

TECHNICAL FIELD

This patent document relates to flow cytometry systems, devices, and processes.

BACKGROUND

Flow cytometry is a technique used for measuring and characterizing individual particles or cells. Flow cytometers can include fluidic systems coupled with optics and/or electronics to analyze characteristics of the particles or cells as move through the fluidic system.

SUMMARY

Techniques, systems, and devices are described for spatially and temporally transforming signals detected by flow cytometers to provide images of the individual particles or cells in flow cytometry.

In one aspect, a method for imaging particles in flow cytometry includes transmitting a light beam at a fluidic channel carrying a fluid sample containing particles, such that the light beam is scattered by the particles or causes fluorescent emission from the particles in the fluidic channel; receiving the scattered or fluorescently-emitted light at a spatial optical filter, the spatial optical filter including a surface having a plurality of apertures arranged in a pattern along a transverse direction opposite to particle flow and a longitudinal direction parallel to particle flow, such that different portions of a particle flowing over the pattern of the apertures pass different apertures at different times and scatter the light beam or emit fluorescent light at locations associated with the apertures; encoding an optical signal including spatial and temporal information of the particle based on at least some of the received scattered or emitted fluorescent light from the fluidic channel carrying the fluid sample; detecting the encoded optical signal by an optical detector; and processing the detected optical signal, at a data processing unit in communication with the optical detector, to produce image data associated with the particle flowing through the fluidic channel, in which the produced image data includes information of a physical characteristic of the particle.

In one aspect, an imaging flow cytometer system includes a fluidic device structured to include a substrate and a fluidic channel disposed on the substrate to carry a fluid sample containing particles along a particle flow direction; a light source to generate a light beam at the fluidic channel to illuminate the fluid sample, in which, when illuminated by the light beam, light is scattered by the particles or causes fluorescent emission from the particles; an optical detector arranged in an optical path of the scattered or fluorescently-emitted light; an optical filter positioned in an imaging plane of the optical detector and structured to include a surface having a plurality of apertures arranged in a pattern along a transverse direction opposite to and a longitudinal direction parallel to the particle flow direction, such that different portions of a particle flowing over the pattern of the apertures pass different apertures at different times and scatter the light beam or emit fluorescent light at locations associated with the apertures, in which the optical filter is operable to encode an optical signal including spatial and temporal information of the particle based on at least some of the received scattered or emitted fluorescent light from the fluidic channel carrying the fluid sample, such that the encoded optical signal is detected by the optical detector; and a data processing unit in communication with the optical detector, the data processing unit to process the encoded optical signal to produce image data associated with the particle flowing through the fluidic channel, in which the produced image data includes information of a physical characteristic of the particle.

In one aspect, an optical spatial filter for encoding an optical signal from particles flowing in a fluidic channel includes a substrate having a plurality of apertures arranged in a pattern along a transverse direction opposite to and a longitudinal direction parallel to a particle flow direction of the particles flowing in the fluidic channel, in which the optical spatial filter is operable to encode the optical signal from the particle flowing in the fluidic channel when positioned in an optical path between an illumination region of the fluidic channel upon which a light beam illuminates and an optical detector, in which the optical spatial filter is positioned in an imaging plane of the optical detector, in which the optical spatial filter is operable to encode the optical signal based on different portions of a particle flowing over the pattern of the apertures pass different apertures at different times and scatter the light beam or emit fluorescent light at locations associated with the apertures, in which the encoded optical signal includes spatial and temporal information of the particle based on at least some of the received scattered or emitted fluorescent light from the fluidic channel.

The subject matter described in this patent document can be implemented in specific ways that provide one or more of the following features. For example, the disclosed systems, devices, and methods include engineered spatial filters and signal processing techniques to give flow cytometers imaging capabilities. For example, the disclosed technology can provide high quality images of fast moving cells in a flow cytometer that are obtained using photomultiplier tube (PMT) detectors, e.g., capable of obtaining high throughput in manners fully compatible with existing cytometers, and which can be employed instead of conventional CCDs or any megapixel cameras found in many imaging systems. The disclosed technology can be applied to retrofit traditional flow cytometers to become imaging flow cytometers at a minimum cost. Exemplary results of implementations using the disclosed technology demonstrate the imaging of cells travelling at a velocity of 0.2 m/s in a microfluidic channel, corresponding to a throughput of approximately 1,000 cells per second.

BRIEF DESCRIPTION OF THE DRAWINGS

FIGS. 3A-3C show data plots presenting a comparison of spatial filter based flow cytometry imaging and wide-field fluorescent imaging.

DETAILED DESCRIPTION

Figure 1A:
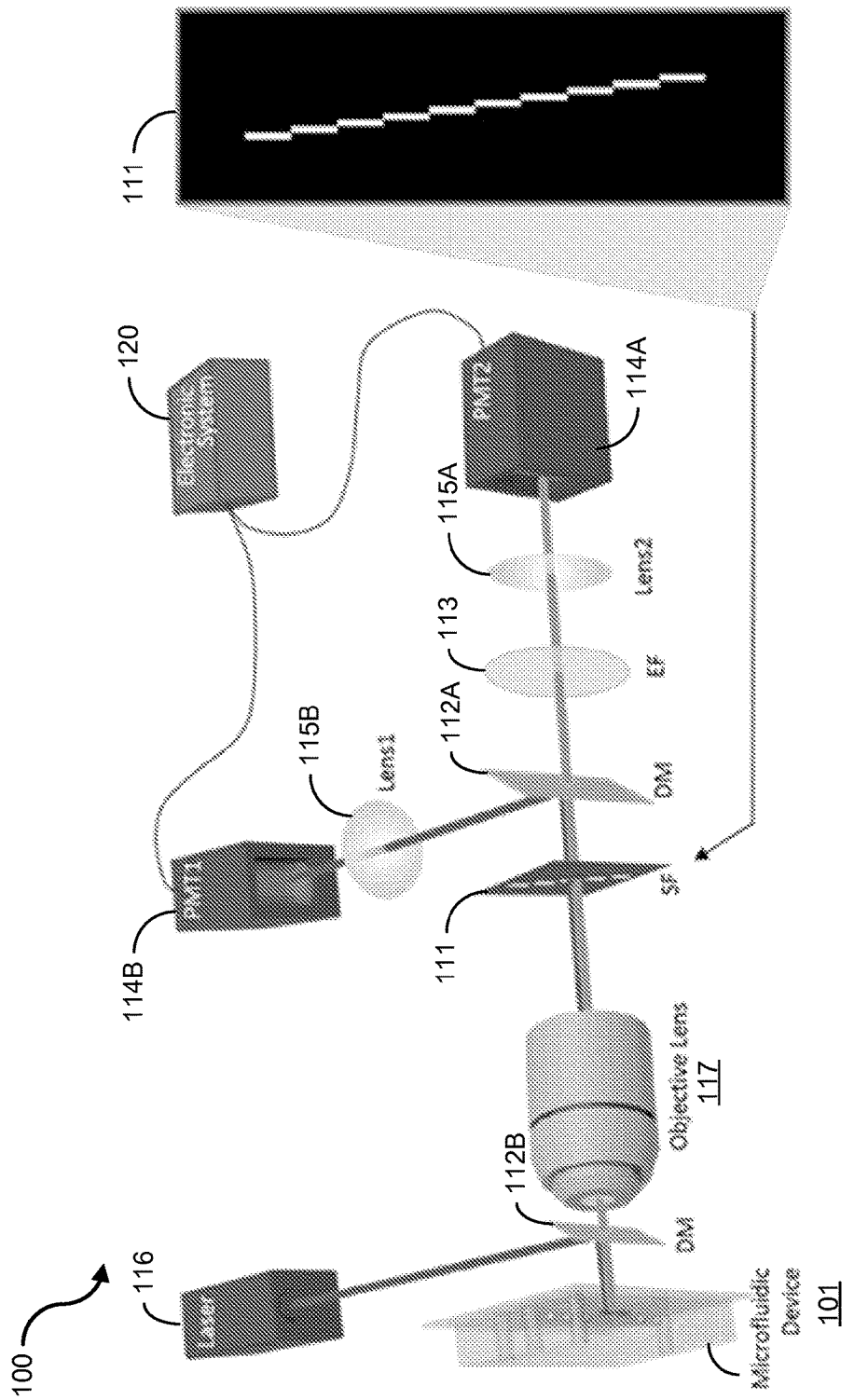
FIGS. 1A and 1B show illustrative diagrams of an exemplary imaging flow cytometer system of the disclosed technology.

Flow cytometry can be used to analyze multiple physical characteristics of a large population of single cells as cells flow in a fluid stream through an excitation light beam. In some applications, flow cytometers measure fluorescence and light scattering from which information about the biological and physical properties of individual cells are obtained. Although flow cytometers have massive statistical power due to their single cell resolution and high throughput, they produce no information about cell morphology or spatial resolution offered by other characterizations such as microscopy. The ability to determine cell morphology and/or spatial resolution would be a valuable feature in flow cytometers. The disclosed technology provides flow cytometers with cell imaging capabilities.

Techniques, systems, and devices are described for spatially and temporally transforming signals detected by flow cytometers to provide images of the individual particles or cells in flow cytometry.

The disclosed technology includes using engineered spatial filters and data processing techniques to give flow cytometers imaging capabilities. For example, the disclosed technology can provide high quality images of fast moving cells in a flow cytometer that are obtained using photomultiplier tube (PMT) detectors, e.g., capable of obtaining high throughput in manners fully compatible with existing cytometers, and which can be employed instead of conventional CCDs or any megapixel cameras found in many imaging systems. The disclosed technology can be applied to retrofit traditional flow cytometers to become imaging flow cytometers at a minimum cost. Exemplary results of implementations using the disclosed technology demonstrate the imaging of cells travelling at a velocity of 0.2 m/s in a microfluidic channel, corresponding to a throughput of approximately 1,000 cells per second.

Background and Introduction of the Present Technology

Cell imaging and high throughput single cell analysis are among some of the primary techniques for studies of cell and molecular biology and medicine. Microscopy is considered an important imaging tool in biology and medicine and has capabilities to generate cell images of extraordinary details, e.g., such as fluorescent images from specific macromolecules, organelles, or subunits of the cells. Yet a microscope yields information via imaging at a relatively low throughput. Given the heterogeneous properties of biological objects such as cancer cells and cells going through different stage of life cycles, much improved understanding of cell and tissue properties can be achieved from the individual properties of a very large population (e.g., thousands to millions) of cells. The limited throughput of microscopy techniques has become an impediment for studies of the heterogeneous characteristics of biological samples.

Flow cytometry is a powerful tool supporting very high throughput analysis, enabling detection of single cell properties at rates from hundreds of cells per second to over 100,000 cells per second. Flow cytometers can measure and analyze multiple physical parameters of cells, including a cell's relative size, nuclear granularity, and fluorescence from specific markers or constituents, as each cell in a fluid stream flows through a region of optical interrogation area illuminated by light beams, e.g., laser beams. However, conventional flow cytometers do not produce the spatial resolution as microscopy does to allow detailed investigation of cell properties that are needed in many applications. As an illustrative analogy, flow cytometers can quickly tell male from female over a large group of people without being able to recognize the facial features of each individual, whereas imaging cytometers can reveal the detailed facial features of each person but cannot perform the function fast enough to a large number of people that need to be investigated.

In spite of the above constraint, flow cytometers have been extensively used in biomedical research and playing an increasing role in clinics because of their advantage of high throughput, single cell resolution, and compatibility with cell sorting capabilities. However, the lack of high spatial resolution that contains valuable phenotypical and morphological information crucial to diagnosis and cell analysis is a disadvantage of present flow cytometry techniques, and provides strong incentive to incorporate imaging capabilities into flow cytometry. Flow cytometry stands to gain from imaging capabilities that would distinguish characteristics of the particles or cells interrogated in the fluid channels at a high throughput.

To date the only successful effort in this area is the imaging flow cytometer developed by Amnis/Millipore (e.g., ImageStream). Significantly different from all other flow cytometers, the Amnis flow cytometer relies on the time delay and integration (TDI) high-speed charge-coupled device (CCD) camera with a large number of pixels, as opposed to photomultiplier tubes (PMTs) used in almost all today's flow cytometers to take advantage of PMT's high speed and superb sensitivity. The Amnis system is much more costly than conventional flow cytometers, and is not ready for integration of cell sorting capabilities due to its unique operation requirements and optics design. As a result, only a very small number (e.g., <5%) of flow cytometers deployed today has acquired the imaging capabilities in spite of the strong desire for such attractive features in flow cytometers.

The disclosed technology includes a spatial-to-temporal transformation technique that provides imaging capabilities to flow cytometers. In some implementations, for example, a specially designed spatial filter is placed in front of the PMT detector in the flow cytometer to produce a temporal waveform of the fluorescent or scattering signal. This waveform, encoded by the spatial filter, contains all the information needed to map out the spatial distribution of the signal of a cell, thus allowing construction of the cell image from the temporal waveform. The exemplary design is compatible with the existing optic design of conventional flow cytometers, and can be easily implemented to upgrade a conventional flow cytometer to become one with cell imaging capabilities at minimum cost. Exemplary implementations of the disclosed technology were performed and described here, which show single cell images of A549 human lung adenocarcinoma epithelial cells in an exemplary flow cytometer device of the present technology (e.g., shown in FIG. 1A). In such examples, the flow speed of the cells is 0.2 m/s, corresponding to a throughput of approximately 1,000 cells per second. The disclosed technology is advantageous over existing megapixel imaging devices. For example, CCD- or CMOS-based technology adopted by nearly all imaging systems today require a relatively long integration time (or exposure time) to capture pictures frame by frame and therefore has speed limitation for imaging cells travelling at high speed.

In one aspect, a method of imaging a particle in a flow cytometer includes transmitting a light beam at a fluidic channel to illuminate a fluid sample containing particles to affect the light (e.g., scatter or emit) to be received by a pattern of apertures spatially arranged about the fluidic channel, in which the pattern of apertures includes a substrate structured to form a plurality of slits arranged on the substrate such that different portions of a particle flowing across the pattern of apertures will pass different slits at different times and scatter the light beam to produce optical scattering signals or emit the light (e.g., fluorescent emission) to produce optical emitted signals, encoding an optical signal from the optical scattering or emitted signals based on the pattern of apertures, in which the encoded waveform includes spatial and temporal information of the particles, and detecting the encoded optical signal to produce image data associated with the particles.

Exemplary Embodiments of the Present Technology

Figure 1B:
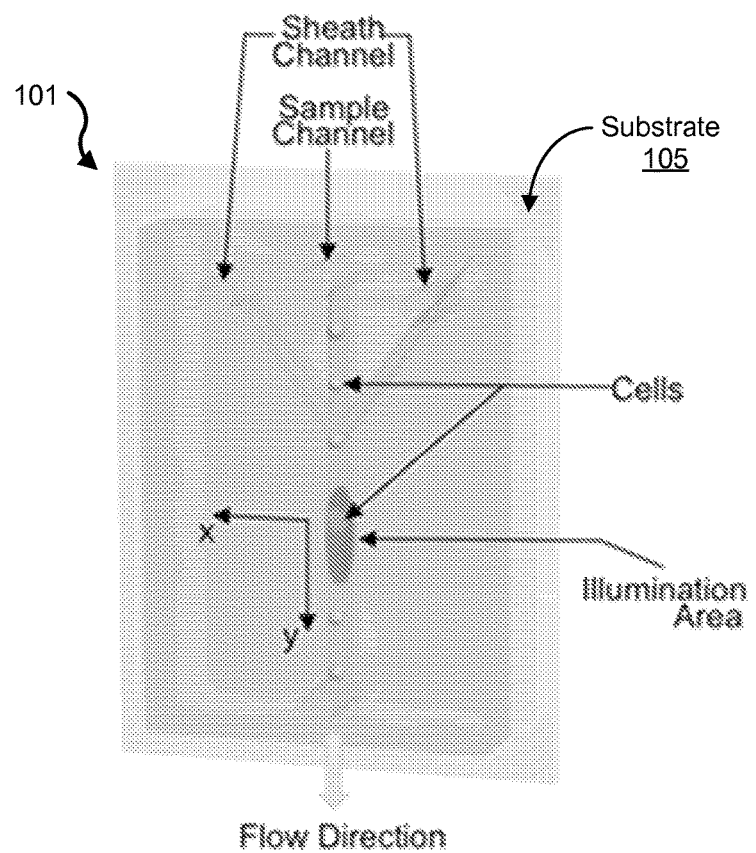

Exemplary embodiments of imaging flow cytometer devices, systems and methods of the present technology are disclosed. FIGS. 1A and 1B show diagrams of an exemplary imaging flow cytometer system 100. The system 100 includes a fluidic system including a microfluidic device or chip 101 for introducing cells into a fluidic channel (e.g., microfluidic channel having a microscale dimension), an optical system for illumination and detection of the light signals, and an electronic system 120 for data acquisition and processing. The optical system of the imaging flow cytometer system 100 includes a dichroic mirror (DM) 112, a spatial filter (SF) 111, an optical source emitter (e.g., laser) 116; and one or more photomultiplier tubes (PMT) 114 in electrical communication with the electronic system 120.

As shown in the example of FIG. 1A, the optical system of the imaging flow cytometry system 100 is configured such that the optical source emitter 116 is operable to emit light at a dichroic mirror 112B that directs the light at an illumination area in the fluidic channel of the microfluidic device 101. For example, the light source 116 can include a laser, e.g., a semiconductor laser diode, or a Hg-arc lamp, among other light sources. The optical system of the imaging flow cytometry system 100 is configured to such that the spatial filter 111 is arranged in the optical path of reflected light from the illumination area of the microfluidic device 101 to receive the emitted and/or scattered light (e.g., fluorescence emission and backscattering light) from the sample and to encode the received light based on the pattern of openings of the spatial filter 111. In some implementations, for example, the optical system can include an objective lens 117 configured in the optical path to receive the reflected light from the illumination area of the microfluidic device 101 to focus the reflected light onto the spatial filter 111. The encoded light is passed from the spatial filter 111 to a second DM 112A, which directs the encoded light in one or more optical paths toward a PMT or multiple individual PMTs in a wide-field fluorescence microscope configuration. In the example embodiment shown in FIG. 1A, a first PMT 114A is arranged in a first optical path to receive the fluorescence emission of the particles flowing in the fluidic channel, and a second PMT 114B arranged in a second optical path to receive the backscattering signal of the particles flowing in the fluidic channel. For example, the optical system of the imaging flow cytometry system 100 can include an emission filter 113 and a first lens 115A in the first optical path to filter and focus the encoded fluorescent light into the PMT 114A, and a second lens 115B in the second optical path to focus the encoded backscatter light into the PMT 114B.

FIG. 1B shows an illustrative diagram of the microfluidic device 101, which includes the fluidic channel in which suspended cells or particles are carried in a fluid controlled by sheath flow to travel in the center of the fluidic channel at a uniform velocity. The microfluidic device 101 is structured to include a substrate 105, on which the fluidic channel is disposed to carry a fluid sample containing particles (e.g., cells). In some implementations, for example, the substrate 105 can include a substrate base and a bulk material attached to the base, in which the bulk material includes the fluidic channel carved out of the surface in contact with the base. For example, the substrate can include polydimethylsiloxane (PDMS) material. In some implementations, for example, the bulk material can include PDMS and the substrate base can include glass or other rigid electrically insulative material to support the bulk material with the channel. In some implementations, the fluidic channel is structured to have a width and/or height dimension greater than the microscale (e.g., millimeter), whereas in other implementations, the fluidic channel is structured to have a width or a height dimension in the microscale (e.g., micrometers) or less (e.g., nanometers). The following examples refer to the fluidic channel as a microfluidic channel, for example. In some implementations, such as that shown in the diagram of FIG. 1B, the microfluidic channel stems from a plurality of channels, e.g., including a channel to receive and carry the fluid sample containing the particles, and one or more sheath channels. The microfluidic channel of the microfluidic device 101 is structured to transmit a probe light received from the optical system of the imaging flow cytometry system 100, e.g., such as the received laser light from the laser 116. In some embodiments, for example, the spatial filter 111 can be configured on the microfluidic device 101 above the channel at the illumination area.

The spatial filter 111 forms a mask that includes a pattern of openings arranged to optically align with respect to the microfluidic channel. The pattern of openings encodes a waveform based on the probe light transmitted through the microfluidic channel and the pattern design of the spatial filter 111, from which the waveform can be decoded using data processing techniques of the present technology to (i) optically detect of a physical characteristic (e.g., position, size, etc.) of a particle in the microfluidic channel and (ii) form an image of the particle including the physical characteristic. An example spatial filter design of the spatial filter 111 of the system 100 is shown on the right of the diagram of FIG. 1A. The illustration of the spatial filter depicts an engineered spatial filter design that has ten 100 µm by 1 mm slits positioned apart in the way of one is immediately after another in both x-direction (transverse to the flow direction) and y-direction (longitudinal to the flow direction). For example, the 100 µm dimension of the example slit shown in FIG. 1A is in the x-direction; and the 1 mm dimension of the slit is in the y-direction. The x- and y-directions are labeled in FIG. 1B. Alternatively, for example, the spatial filter 111 can have two slits of 100 µm by 1 mm in x- and y-direction, respectively, in front of the slit tandem, in which this example spatial filter design can be applied for precise calculation of cell traveling speed for each cell. In one example, each slit can be configured to have a particular length and width in the longitudinal and transverse dimensions, respectively, such that each slit is positioned on the spatial filter to be immediately outside the longitudinal and transverse coordinate of its adjacent slit. In yet another example, the spatial filter 111 can include a pattern of openings where at least two of the openings have varying longitudinal and transverse dimensions (e.g., diagonal) with respect to a fluid flow direction across the microfluidic channel, such that the encoded waveform carries information including the position of the particle in two dimensions. Some examples of such are shown in U.S. Pat. No. 9,074,978, which is incorporated by reference in its entirety as part of the disclosure in this patent document.

Figure 1C:
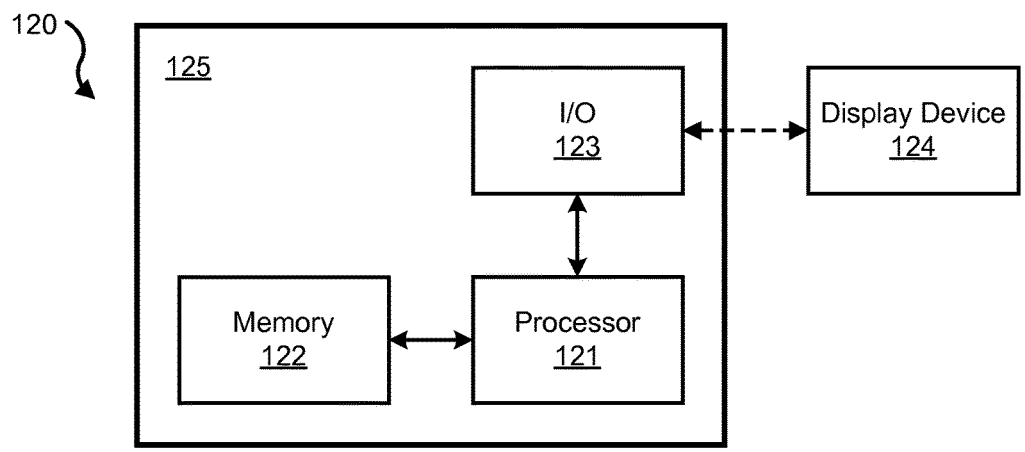
FIG. 1C shows a block diagram of an example electronics system of the imaging flow cytometer system.

FIG. 1C shows a block diagram of an example electronics system 120 of the imaging flow cytometer system 100. The electronics system 120 includes a data processing and communications unit 125 that includes a processor 121 (e.g., such as a central processing unit (CPU) or microcontroller) to process the data obtained by the optical system of the imaging flow cytometer system 100. The data processing and communications unit 125 that includes a memory 122 in communication with the processor 121 to store and/or buffer the data. The data processing and communications unit 125 includes an input/output (I/O) unit 123 in communication with the processor 121 that provides wired and/or wireless interfaces (also referred to as communication interfaces) compatible with typical data communication standards for communication of the computer with other computers and computer systems, or external interfaces, sources of data storage, or display devices (e.g., such as the display device 124 shown in FIG. 1C), among others. For example, the memory 122 can include processor-executable code, which when executed by the processor 121, configures the data processing and communications unit 125 to perform various operations, such as receiving information, commands, and/or data, processing information and data, and transmitting or providing information/data to another entity or to a user. For example, the I/O unit 123 can include a transceiver to provide wired or wireless communications using one or more of the following standard communications interfaces, e.g., including, but not limited to, Universal Serial Bus (USB), IEEE 1394 (Firewire), Bluetooth, Bluetooth Low Energy (BLE), ZigBee, IEEE 802.11 (Wi-Fi), Wireless Local Area Network (WLAN), Wireless Personal Area Network (WPAN), Wireless Wide Area Network (WWANO, WiMAX, IEEE 802.16 (Worldwide Interoperability for Microwave Access (WiMAX)), 3G/4G/5G/LTE cellular communication methods, and parallel interfaces, among others. In some implementations of the system 100, for example, the data processing and communications unit 125 can be in data communication with the optical system to store and manage data associated with the operations of the optical system, e.g., such as parameters, settings, etc.

In an exemplary operation of the imaging flow cytometer of FIG. 1A, for example, the suspended particles (e.g., cells) are introduced into the microfluidic channel and hydrodynamically focused by sheath flow, e.g., ensuring that the cells travel in the center of the fluidic channel at a uniform velocity. The fluorescence emission and backscattering light from the sample are detected by two individual PMTs in a wide-field fluorescence microscope configuration. In this example operation, cells are flown in a microfluidic channel of the microfluidic device, e.g., which can be made of soft-molded PDMS bonded to a glass substrate. To accommodate the geometry of the microfluidic device, the laser beam is introduced to the optical interrogation site in the fluidic channel by a miniature 45-degree dichroic mirror (DM) positioned in front of a 50× objective lens (NA=0.55, working distance=13 mm). The size of the 45-degree dichroic mirror is small enough to allow the backscattering light (147° to 168° with respect to the normal incident light) to bypass the dichroic mirror and enter the objective lens. The disclosed spatial filter, e.g., such as the SF having the pattern shown in FIG. 1A, is inserted in the detection path right at the image plane of the optic system. Both the fluorescent and backscattering light from a travelling cell (or particle) are collected by the objective lens and pass the filter before reaching their respective PMT detectors. Another dichroic mirror (DM) splits the light by its spectrum to route the desired emission bands to the appropriate PMTs. The output of each PMT is sent to a computer system and processed to generate cell images from fluorescence and back scattering. Although the exemplary system depicted in FIG. 1A shows only one PMT for detection of fluorescent signal, it is understood that one can add more PMTs and, if necessary, more excitation laser beams, to produce multicolor fluorescent signals as in any conventional flow cytometers.

Restoring Cell Images from Light Intensity Profiles.

The disclosed technology includes techniques for spatial-to-temporal transformation of the detected signals, which can be represented in the following relation:

$$S(t)=\int_{x,y} Cell(x, y-Mvt) \cdot F(x,y) \cdot I(x,y) dx dy \quad (1)$$

where $S(t)$ is the measured PMT signal, Cell is the two-dimensional cell (or particle) fluorescence or scattering intensity profile, $F(x,y)$ is the characteristic function of the spatial filter, $I(x,y)$ is the intensity profile of laser illumination, y is the cell-travelling direction and x is the transverse direction, and M is the magnification factor of the optical system pertaining to the flow cytometer.

As the cell (or particle) travels in the microfluidic channel at a speed or velocity v, the image projected onto the spatial filter travels at an effective speed of Mv. To simplify the mathematical process of solving for Cell in Equation (1), for example, F(x,y) can be chosen to be a series of rectangle function represented in Equation (3), and I(x,y) can be chosen to be a constant from a laser beam of uniform intensity.

$$F(x, y) = \sum_{x=1}^{N} (u(y - (x-1)L) - u(y - xL)) \quad (2)$$

where x=1, 2, ..., N is the number of rows in the spatial filter, L is the length of the rectangular slit that transmits fluorescent or scattering light. For example, Equation (1) can be rewritten as:

$$S(t) = \sum_{x=1}^{N} \int_y \text{Cell}(x, y - Mvt) \cdot (u(y - (x-1)L) - u(y - xL)) dy \quad (3)$$

For example, one can solve for "Cell" by taking the time derivative of Equation (3)

$$\frac{d}{dt}S(t) = \sum_{x=1}^{N} \frac{d}{dt} \int_{-\infty}^{\infty} \text{Cell}(x, y - Mvt) \cdot (u(y - (x-1)L) - u(y - xL)) dy \quad (4)$$

Assuming the cell orientation does not change within such a short time interval, one can represent Equation (4) as the following:

$$\frac{d}{dt}S(t) = \sum_{x=1}^{N} \int_{-\infty}^{\infty} \text{Cell}(x, y') \cdot \frac{d}{dt} \quad (5)$$

$$(u(y' + Mvt - (x-1)L) - u(y' + Mvt - xL)) dy' =$$

$$\sum_{x=1}^{N} \int_{-\infty}^{\infty} \text{Cell}(x, y') \cdot Mv(\delta(y' + Mvt - (x-1)L) - \delta(y' + Mvt - xL))$$

$$dy' = \sum_{x=1}^{N} \text{Cell}(x, Mvt - (x-1)L) - \sum_{x=1}^{N} \text{Cell}(x, Mvt - xL)$$

To obtain Equation 5, used was y'=y−Mvt. When the cell size does not exceed the slit length L, within the specific time interval $$t \in \left((x_0 - 1)\frac{L}{Mv}, x_0 \frac{L}{Mv}\right), \frac{d}{dt}S_{x_0}(t) = \text{Cell}_{x_0}(y) - \text{Cell}_{x_0-1}(y).$$

As a result, the cell image can be constructed from the following relation:

$$\text{Cell}_{x_0}(y) = \frac{d}{dt}S_{x_0}(t) + \text{Cell}_{x_0-1}(y) \ 1 \le x_0 \le N \quad (6)$$

The detected optical signal includes encoded information based on the specific time and spatial location of the particle at each slit as it passes through the channel. Since the imaging flow cytometer system 100 can measure the speed (v) of the particle flowing in the microfluidic channel of the microfluidic device 101, know the magnification of the optical system (M), and know the characteristic function F(x,y−Mvt) of the slits based on the predetermined slit geometry, the signal produced by each spot over the particle (e.g., a biological cell) can be calculated by deconvolving the measured signal with the known characteristic function F(x,y−Mvt). This calculated "localized signal" from the particle (e.g., cell) is essentially the "image" of the particle. For example, if the measured signal is from light scattering, the reconstructed image after signal processing is the "scattering image" with the "bright areas" being the areas of the strongest scattering efficiency. For example, if the measured signal is produced from fluorescence (e.g., fluorescently labeled protein), then the reconstructed image is the "fluorescent image" showing the local distribution and concentration profile of the labeled protein. For example, if the fluorescently labeled protein is a membrane protein, then the contour of the image gives rise to the cell shape and size. On the other hand, if the cell nucleus is fluorescently labeled, then the constructed image becomes the image of the cell nucleus. By implementing the data (image) processing methods of the present technology, all these different types of images, which represent different properties of the particles (e.g., cells), can be produced, and these produced images can also be overlaid to produce a high-information content image of the flowing particles (e.g., cells).

In some embodiments, for example, the data processing method includes determining a position or a velocity of the particle in at least two dimensions. The data processing method includes determining a characteristic function (e.g., F(x,y−Mvt)) of the spatial optical filter, in which the characteristic function includes parameters associated with size and arrangement of the apertures in the pattern. The data processing method includes determining a localized signal associated with one or more portions of the particle (e.g., regions of the cell) to produce the image data associated with the particle. For example, the data processing method can determine the localized signal data by deconvolving a particle signal with the determined characteristic function, in which the particle signal includes the detected optical signal, the determined position or velocity, a magnification of an optical system to focus the received emitted and/or scattered light at the spatial optical filter.

Generally, the spatial filter is designed in such a manner that, at the image plane, the fluorescence from different parts of the particle (e.g., cell) will pass different slits at different times. As a result, the waveform of the fluorescent signal from the PMT includes a sequence of patterns separated in time domain, and each section of the signal in the time domain corresponds to the fluorescent (emission and/or scattering) signal generated by each particular regime of the cell (or particle). After the light intensity profile over each slit is received, the cell image of the entire cell can be constructed by splicing all the profile together.

In some implementations, for example, a data processing technique for cell image construction can included the expression:

$$\text{Cell}_i(j) = \frac{d}{dt}S_i(t) + \text{Cell}_{i-1}(j) \qquad (7)$$

$$i = 1, 2, \ldots, 10; \, j = 1, 2, \ldots, N$$

where i is the number of row of the constructed cell image, j is the number of column, N is the number of digital sample points of PMT signal from one row, $S_i(t)$ is the PMT signal that represents the light intensity out of the $i^{th}$ row of cell, and $\text{Cell}_i(j)$ is the light intensity corresponding to the $i^{th}$ row and $j^{th}$ column of the cell under test.

For example, in implementations employing a 50× objective lens (M=50) in the system 100, the filter design allows for the construction of the fluorescent or scattering image of a travelling cell of 20 μm×20 μm using the disclosed data processing algorithm described in Equation (6). The data processing techniques of the disclosed technology provide a minimum amount of computations, and are suitable for high-throughput, real-time image-based cell classification and sorting.

The present technology includes a high-throughput, real-time method of imaging particles (e.g., cells) in a flow cytometer, which can be used for particle or cell classification and/or sorting. The method can include transferring a fluid sample containing particles (e.g., cells) into a fluidic channel of a fluidic device (e.g., the device 101). The method includes transmitting a light beam from a light emitter (e.g., the laser 116) at the fluidic channel carrying the fluid sample containing the particles (e.g., cells), such that the light beam is affected by (e.g., scattered) and/or affects (e.g., causes fluorescent emission of) the particles in the fluidic channel. The method includes receiving the scattered or fluorescent-emitted light (e.g., by focusing via the objective lens 117) at a spatial optical filter (e.g., spatial filter 111). For example, the spatial optical filter includes a surface having a plurality of apertures (e.g., slits) of a predetermined geometry and arrangement on spatial optical filter, in which the pattern of apertures is along a transverse direction opposite to particle flow and a longitudinal direction parallel to particle flow, such that different portions of a particle (e.g., any particle) flowing across the pattern of the apertures pass different apertures at different times and scatter the light beam or emit fluorescent light at locations associated with the apertures, e.g., which can produce optical scattering or emission signals carrying information about the particles. The method includes encoding an optical signal including spatial and temporal information of the particles based on at least some of the received scattered light from the fluidic channel carrying the fluid sample. The method includes detecting the encoded optical signal by an optical detector (e.g., the one or more PMTs 114). The method includes processing the detected optical signal to produce image data associated with the particle flowing through the fluidic channel, in which the produced image data includes information of a physical characteristic of the particle. For example, the physical characteristic of the particles in the determined image data can include a size of the particle (e.g., in at least two dimensions), a spatial feature or geometry of the particle (e.g., in at least two dimensions), a location and/or concentration of internal features or structures of the particle (e.g., in at least two dimensions), e.g., such as cellular organelles like the nucleus, mitochondria, or a parasitic substance (e.g., virus, toxin, or other non-native substance) in a cell.

Implementations of the method can include one or more of the following features. In some implementations, for example, the method further includes forming an image of the particle based on the produced image data, in which the image includes a visual presentation of the physical characteristic of the particle. In some implementations of the method, for example, the processing the detected optical signal is in real-time as the particles flow in the fluidic channel. In some implementations of method, for example, the processing the detected optical signal includes: determining a position or a velocity of the particle in at least two dimensions; determining a characteristic function of the spatial optical filter, the characteristic function including parameters associated with size and arrangement of the apertures in the pattern; and determining a localized signal associated with one or more portions of the particle to produce the image data associated with the particle by deconvolving a particle signal with the determined characteristic function, in which the particle signal includes the detected optical signal, the determined position or velocity, a magnification of an optical system to focus the received scattered or fluorescently-emitted light at the spatial optical filter. In some implementations, for example, the method further includes sorting the particles based on the determined physical characteristic of the particles. For example, in some implementations of the method, the pattern of apertures includes two or more slits positioned apart such that an adjacent slit is positioned outside a coverage area of a slit with respect to both a longitudinal direction of particle flow in the fluidic channel (y-direction) and a transverse direction perpendicular to the longitudinal direction (x-direction). For example, in some implementations of the method, the pattern of apertures includes ten 100 μm by 1 mm slits. For example, in some implementations of the method, the pattern of apertures includes groups of slits, in which each group of slits includes three parallel arrays of slits that are shifted and spatially isolated and non-overlapping in a longitudinal direction of particle flow in the fluidic channel (y-direction). For example, in some implementations of the method, the light beam includes a laser beam. For example, in some implementations of the method, the optical detector includes a photomultiplier tubes (PMT). For example, in some implementations of the method, the optical detector includes multiple PMTs, where the encoded optical signal is split into multiple optical paths corresponding to the multiple PMTs.

Exemplary Implementations

Figure 2A:
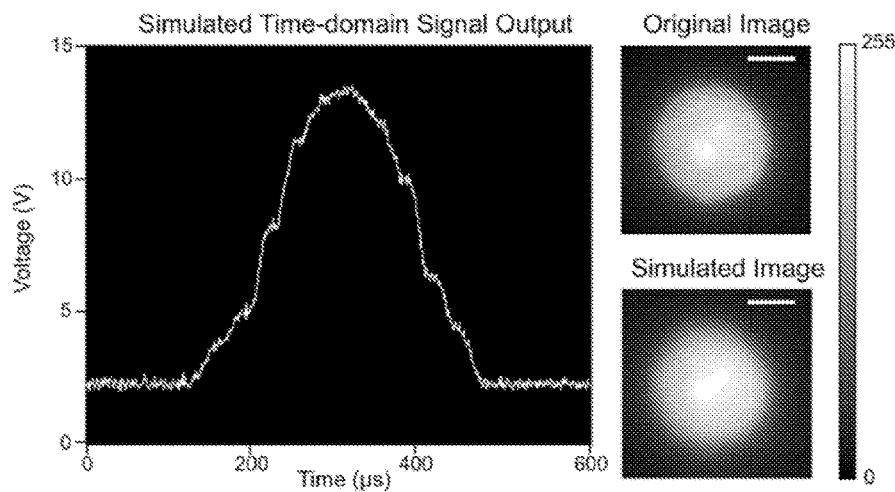
FIGS. 2A and 2B show data plots and diagrams of restoring cell images from photomultiplier tube (PMT) signals.
Figure 2B:
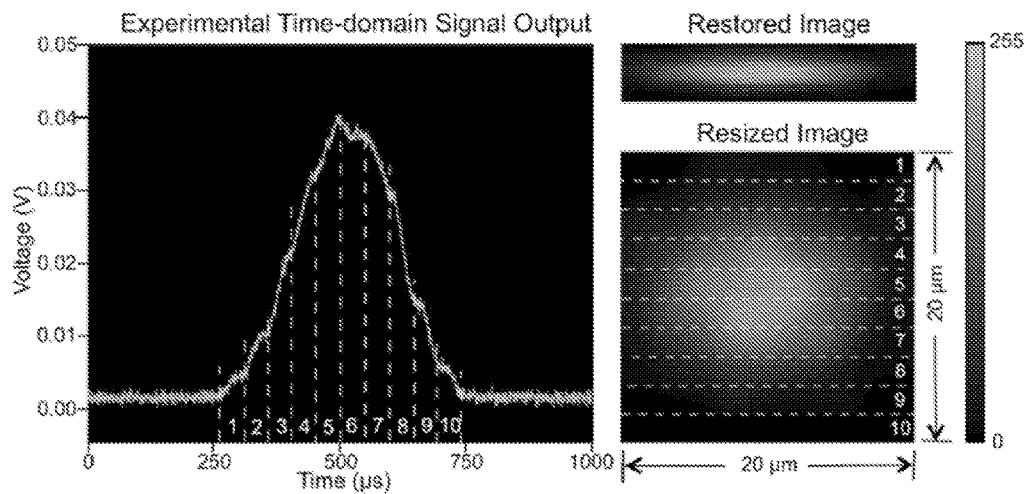

Exemplary implementations were performed to demonstrate this approach by simulation, in which a cell image was used as the cell under test, and the cell traveled through an illumination beam spot at a speed of 0.24 m/s, and by implementations. FIGS. 2A and 2B show data plots and diagrams of restoring cell images from PMT signals. FIG. 2A shows exemplary simulation results: time-domain light intensity signal, original cell image used for simulation, and corresponding restored image. The exemplary scale bar shown in FIG. 2A is 5 μm. The fluorescence light that passes the slits on the spatial filter is sampled at a rate of 500 kHz. For example, the original cell image is shown in FIG. 2A, as well as the time-domain output signal through the spatial filter, and the restored cell image using the exemplary data processing technique and algorithm. Compared to the original cell image, for example, the restored image from simulation shows identical features. It is noted, for example, that the restored image includes a resolution of around 1.5 μm, and the image blur is mainly due to the sampling rate limit and the light diffraction.

During the exemplary implementations, once the cells were injected into the microfluidic channel, a two-slit filter was inserted at the image plane to determine the cell travelling velocity, followed by applying the aforementioned spatial filter. The time-domain signal for each cell was captured by thresholding the PMT readout. FIG. 2B shows exemplary experimental results: time-domain PMT output signal of fluorescent light from an A549 cell stained with CellTrace CF SE, and restored fluorescence image by segmenting and splicing the light intensity profile. The size is labeled in figure. FIG. 2B shows the experimental result of a typical PMT signal and the fluorescence cell image constructed from the PMT signal using Eq. (6). For example, the spatial resolution of the restored image in x-(transverse) direction depends on the number of the slits on the spatial filter, and in y- (cell travelling) direction depends on the sampling rate and cell flow rate. In this exemplary implementation, for example, using a 50×/0.55 NA objective lens, 500 kHz sampling rate for acquiring PMT signal, and 0.2 m/s cell travelling speed, the effective size of the pixel in y-direction was determined to be 0.4 μm $$\left(e.g., \frac{L}{(L/Mv) \times R} = \frac{Mv}{R} = 0.4 \text{ μm}\right),$$

which is smaller than the Rayleigh Criterion, thus resulting in a diffraction-limited resolution in y-direction. For example, the 0.2 m/s cell travelling speed is given by 12 μL/min sample flow rate and 120 μL/min sheath flow rate. As shown in FIG. 2B, in the original image restored by the imaging flow cytometer, the effective pixel size is 2 μm in x-direction and about 0.4 μm in y-direction. The recovered image was then resized to be 80 pixels by 80 pixels to better represent a 20 μm by 20 μm area in the object plane in the microfluidic channel.

The imaging flow cytometer system enables fast fluorescence imaging using only a single PMT instead of pixelated CCD.

FIGS. 3A-3C show data plots showing a comparison of spatial filter based flow cytometry imaging and wide-field fluorescent imaging. In these exemplary data, all images are of A549 human lung adenocarcinoma epithelial cells, stained with CellTrace CF SE. FIG. 3A depicts a data plot representative of the exemplary imaging flow cytometer reconstructed fluorescence images of cells flowing at a velocity of 20 cm/s. FIG. 3B depicts a data plot representative of wide-field fluorescence images of stationary A549 cells. FIG. 3C shows representative confocal microscope images of stationary A549 cells, e.g., in which the objective lens used was 63×/1.30. For FIGS. 3A, 3B, and 3C, the sizes of all images were cropped to 20 μm by 20 μm; and the example scale bar is 5 μm.

The data plot of FIG. 3A shows representative fluorescence images of fluorescently labeled A549 cells flown at 0.2 m/s in a microfluidic channel, producing a throughput of around 1,000 cells/s. For comparison, the data plot of FIG. 3B shows images of the stationary fluorescently labeled A549 cells between a glass slide and a coverslip captured by a fluorescent microscope with a CCD camera under at least 50 ms exposure time. The data plot of FIG. 3C shows images from same batch by a confocal microscope. The resulting images from the imaging flow cytometer appear to be similar to the images of still cells from a fluorescence microscope, even though in the imaging flow cytometer, the cells are travelling at a speed of 0.2 m/s and the signals that give rise to the cell images are detected by a single PMT in a setup and configuration compatible with conventional flow cytometers.

Table 1 shows comparisons in size and shape descriptors of cell images acquired by the exemplary imaging flow cytometer system and fluorescence microscope. Based on 100 cell fluorescence images randomly picked from each group, for example, the measured cell size, circularity, and solidity of the images restored by the imaging flow cytometer are highly consistent with the images taken by the fluorescence microscope, with exception of the aspect ratio defined as the ratio of the major axis to the minor axis of the fitted ellipse. The appreciable difference in the cell aspect ratio between the imaging flow cytometer and fluorescent microscopy may be attributed to cell deformation by the fluidic dynamic shear stress, carrying information about cell stiffness, a property of biological significance.

TABLE 1

| Cell | Area (um 2) | | Circularity | | Solidity | | Aspect Ratio | |
|---|---|---|---|---|---|---|---|---|
| Images from | Mean | St. D. | Mean | St. D. | Mean | St. D. | Mean | St. D. |
| Imaging Flow Cytometer | 126.77 | 3.199 | 0.82 | 0.028 | 0.96 | 0.007 | 1.52 | 0.088 |
| Fluorescence Microscope | 128.74 | 4.511 | 0.87 | 0.048 | 0.96 | 0.013 | 1.08 | 0.064 |

Backscattering Image.

The disclosed spatial-temporal transformation technique is not restricted to specific modes of signals. In the following, it is shown that the approach is capable of combining fluorescence images with backscattering images. The backscattering images captured by the exemplary imaging flow cytometer system reveal the unique properties of cell nuclei as effective markers for applications such as disease diagnosis, cell classification, and cell cycle monitoring. Cellular components with higher concentration of macromolecules exhibit a higher refractive index than the background. These refractive index variations will scatter light when the cell is illuminated by visible light. The size and refractive index distributions of the scattering regions determine the angular distributions of the scattered light. The majority of human cancers originate in the epithelial cells, so the backscattering imagery can potentially benefit the diagnosis of early cancer and intra-epithelial neoplastic changes. To demonstrate the feasibility of the backscattering imaging function for cell nucleus monitoring, A549 cells that are going through different life cycles are tested using the imaging flow cytometer.

To observe cells in different stages, A549 cells were cultured with inhibitors to stop their growth at different development stages. Mitomycin is used to stop the cell growth at G1 phase where the biosynthetic activities of cells are activated to form necessary proteins for the next phase (S phase). Separately, nocodazole is used to arrest the A549 cells at G2/M phase, more specifically at the prometaphase. Being arrested at the prometaphase, the nuclear membrane breaks down and the constituents of nucleus are distributed within the cytoplasm. Lacking a well-defined nucleus confined by the nucleus membrane, the cell has generally stronger but no well-defined contour in light scattering.

Figure 4:
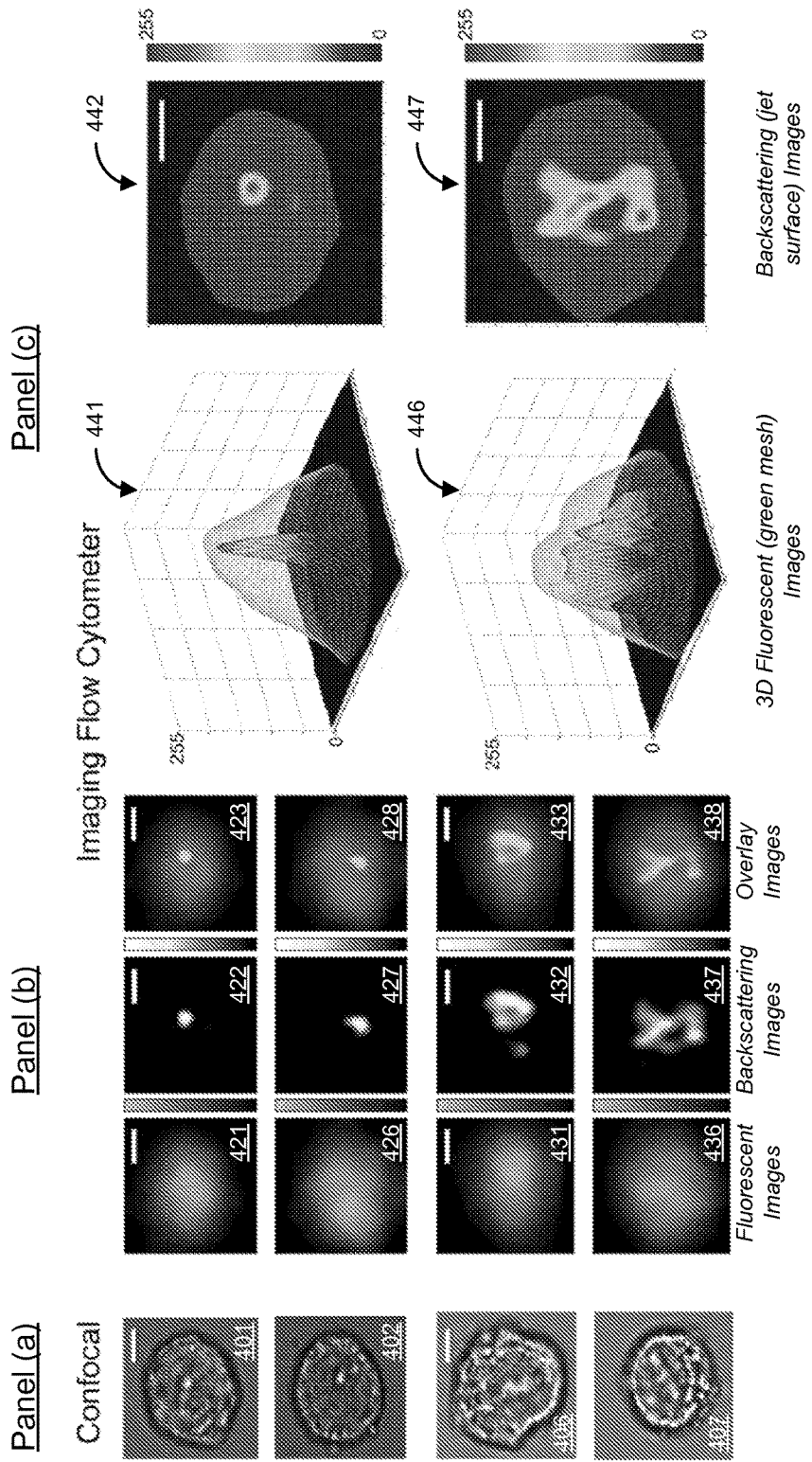
FIG. 4 shows exemplary data of backscattering cell images from the disclosed spatial filter based imaging flow cytometry.

FIG. 4 shows exemplary data of backscattering cell images from the disclosed spatial filter based imaging flow cytometry. The exemplary images are of A549 human lung adenocarcinoma epithelial cells, stained with CellTrace CFSE, flowing at a velocity of 20 cm/s. Panel (a) of FIG. 4 shows representative confocal images of stationary cells arrested at G1 phase (top two, labeled images 401 and 402) and prometaphase G2/M (bottom two, labeled images 406 and 407) arrested cells. Panel (b) of FIG. 4 shows representative imaging flow cytometer images of G1 (top two rows, labeled images 421, 422, 423, 426, 427 and 428) and G2/M (bottom two rows, labeled images 431, 432, 433, 436, 437 and 438) arrested cells. Fluorescence images are shown in left column, backscattering images are shown in middle column, and overlay images are shown in right column. The fluorescence images, backscattering images, and superposition of these two images in panel (b) of FIG. 4 represent the travelling cells (e.g., 0.2 m/s) in the exemplary imaging flow cytometer system 100, as shown in FIG. 1A.

Images acquired by both systems show the general characteristics that cells arrested at G1 phase possess a clearly defined scattering center from the nucleus. In contrast, cells at prometaphase show overall stronger scattering intensities because of higher concentration of nucleic acids and proteins but no well-defined scattering center due to lack of nuclear membrane.

To embody the volume of the scattering cellular components within the cells that are arrested at specific phases, 3-dimensional contour plots for backscattering images overlaid on the fluorescence images are shown in panel (c) of FIG. 4. Panel (c) of FIG. 4 shows 3-dimensional plots for overlay of fluorescence (green mesh) and backscattering (jet surface) images of G1 (top, labeled images 441 and 442) and G2/M (bottom, labeled images 446 and 447) arrested cells. Size of all image crops is 20 µm by 20 µm, all scale bars are 5 µm. Again both the backscattering images from the method of spatial-temporal transformation and the confocal images show consistent subcellular features: cells at G1 phase have a condensed scattering center; and cells at prometaphase have a more distributed scattering region.

For traditional flow cytometry, for example, a histogram is one common way to provide information about a cell population or subpopulation. The parameter associated with the histogram includes fluorescence or scattering intensity. Yet it would be more informative if an image of every single cell under test is available for flow cytometry tests, so that making decisions about gating can be no longer 'blind' to the sample attributes. Moreover, not only the light intensity can be quantified, but also many morphological measurements can be performed on account of the available images of the cells under tests.

Figure 5A:
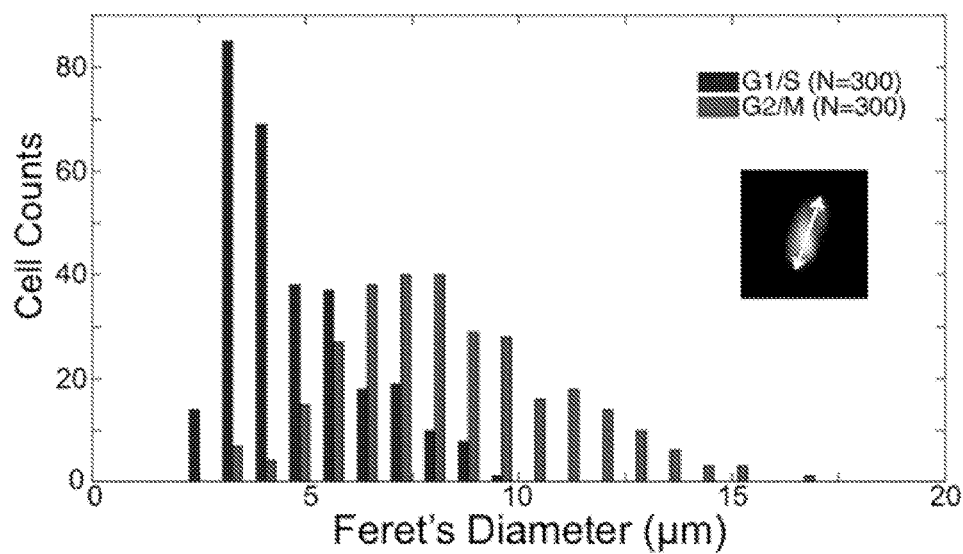
FIG. 5A shows a histograms of the Feret's diameter, also known as maximum caliper, for an example implementation of the imaging flow cytometer system.
Figure 5B:
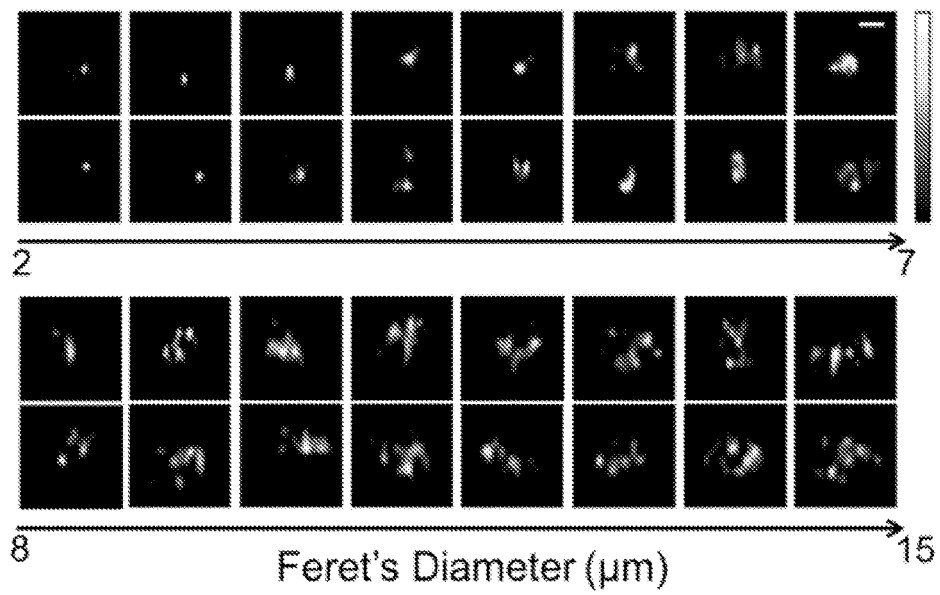
FIG. 5B shows two example backscattering images for each bin from 2 µm to 15 µm in the histogram of FIG. 5A.

FIGS. 5A and 5B demonstrate differences of the backscattering images of cell arrested at G1 phase and G2/M phase. All data and images of FIGS. 5A and 5B are of A549 cells flowing at a velocity of 0.2 m/s. To compare the backscattering images of cells arrested at G1 and G2/M phase, FIG. 5A shows the histogram of the Feret's diameter, also known as maximum caliper. The inset image in the histogram of FIG. 5A includes an arrow illustrating the definition of the Feret's diameter: the longest distance between any two points along the object's boundary. For example, 300 cell images from each group are measured. The G1 cells, shown in blue bars (left bars of bar graph pairs), were shown to have Feret's diameter of approximately 3 to 4 µm. The G2/M cells, shown in red bars (right bars of the bar graph pairs), were shown to have larger Feret's diameter. Instead of pure numerical expression, FIG. 5B shows two example backscattering images for each bin from 2 µm to 15 µm in the histogram. In FIG. 5B, the hot color-bar represents intensity from 0 to 255. All sizes of all cell backscattering images are 20 µm by 20 µm; and the example scale bars is 5 µm.

Exemplary Embodiments of the Present Technology

In some implementations, for example, the exemplary design of spatial filter shown in FIG. 1A can be accompanied by a 200 µm long laser illumination regime that limits the device throughput and sensitivity due to the overall length of the filter in the direction of cell flow (y-direction). To reduce the probability of co-incident event, which occurs when the second cell enters the filter area before the first cell leaves the area, at the particle flow is operated at a reduced sample density. It is noted, for example, that the extended illumination area (e.g., because of the long filter) may also reduce the fluorescent intensity and affect the sensitivity of the system.

There are several ways to overcome the above constraint with a modified spatial filter design. One such design is Phase-Shifted Spatial Filter (PSSF) that can significantly shorten the overall filter length to achieve enhanced throughput and sensitivity.

Phase-Shifted Spatial Filter.

Figure 6:
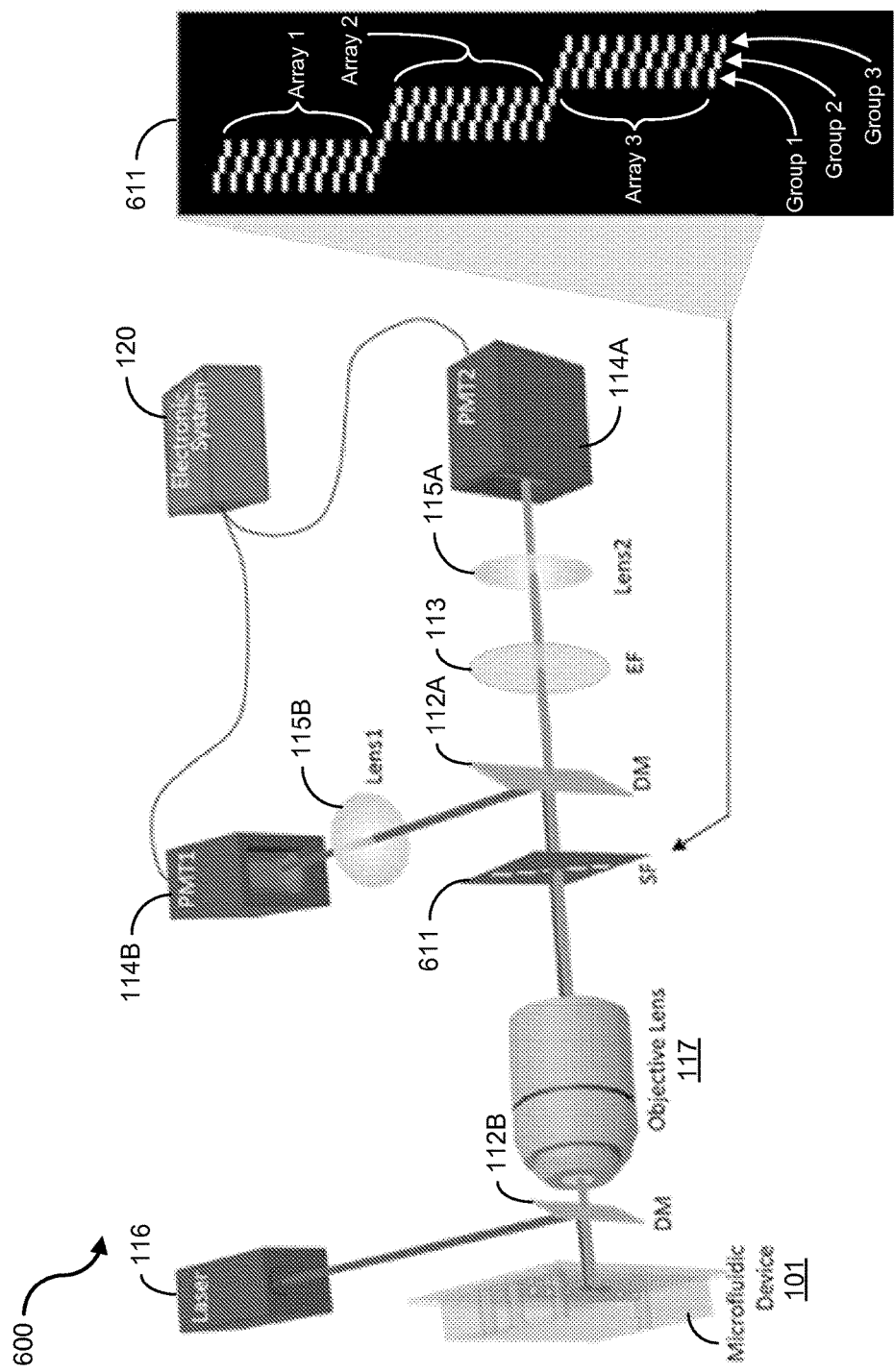
FIG. 6 shows a diagram depicting an exemplary imaging flow cytometer of the disclosed technology using phase-shifted spatial filter (PSSF).

FIG. 6 shows another exemplary embodiment of the disclosed imaging flow cytometer system 600. The system 600 includes the features of the system 100, but instead of the spatial filter 111, the system 600 includes an exemplary phase-shifted spatial filter (PSSF) 611 in the optical system arrangement. The spatial filter 611 includes groups of slits, in which each group of slits includes multiple parallel arrays of slits that share the same periods and are shifted in the cell travelling direction (longitudinal or y-direction). The example spatial filter 611 shown in FIG. 6 includes three parallel arrays of slits per group, array 1, array 2, and array 3. The phase shift is designed in a manner that all slits are spatially isolated (non-overlapping) in y-direction. As a result, when a cell travels through the filter area, the PMT records all the light intensity changes when the fluorescent light out of the cell passes one more/less slit. The light intensity profile from a cell then can be derived as following:

$$\text{Cell}_g(h) = \frac{d}{dt} S_g(t) + \text{Cell}_{g-1}(h) \tag{8}$$

$$g = 1, 2, 3; h = 1, 2, \ldots, N$$

where g is the number of the group seeing from the cell entering side to the cell exiting side, h is the number of column in one group, N is the number of digital sample points of PMT signal from one group, $S_g(t)$ is the PMT signal crop that represents the light intensity out of $g^{th}$ group of cell, and $\text{Cell}_g(h)$ is the light intensity corresponding to the $g^{th}$ group and $h^{th}$ column of the cell of interest.

After obtaining the light intensity profile for one group of regime of the cell, one can reconstruct the cell image by assigning the intensity value to corresponding row as follows:

$$\text{Cell}_i(j) = \text{Cell}_g(3*C+i) \ C=0,1,2,\ldots \text{ constant} \tag{9}$$

where i is the number of row within the gth group, and j is the number of column of one row.

Using this method, the throughput can be three-times higher than the spatial filter discussed previously since there are three rows of slits in one group. The required illumination area also can be shrunk by the same factor, yielding 3X higher effective laser intensity for enhanced sensitivity of the system.

Spatial Filter with Frequency Modulation.

Figure 7:
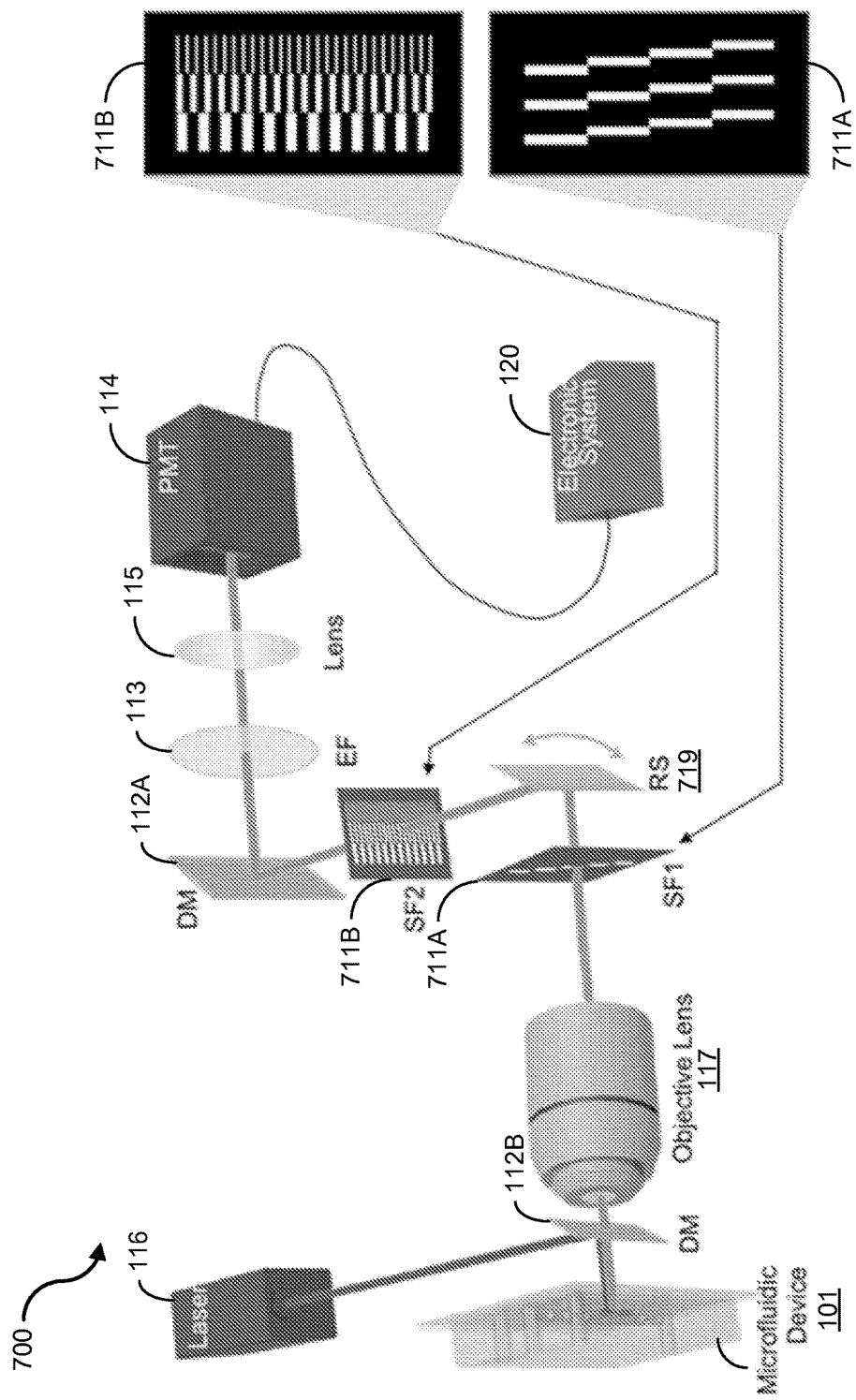
FIG. 7 shows a diagram depicting an exemplary imaging flow cytometer of the disclosed technology using a spatial filter configuration with frequency modulation.

Another method to reduce the spatial filter length is frequency modulation. FIG. 7 shows a diagram depicting an exemplary imaging flow cytometer system 700 of the disclosed technology using a spatial filter configuration with frequency modulation. Like the system 100, the system 700 includes a fluidic system including the microfluidic device or chip 101 for introducing cells into a microfluidic channel, an optical system for illumination and detection of the light signals including a spatial filter set with frequency modulation, and the electronic system 120 for data acquisition and processing. The imaging flow cytometer system 700 includes the dichroic mirror (DM) 112B, two spatial filters (SF1 and SF2) 711a and 711B, an optical light source emitter (e.g., laser 116), and a photomultiplier tube (PMT) 114. As shown in the example of FIG. 7, the optical system of the imaging flow cytometry system 700 is configured such that the laser 116 is operable to emit light at the dichroic mirror 112B that directs the light at the illumination area in the microfluidic channel of the microfluidic device 101. The optical system of the imaging flow cytometry system 700 is configured to such that the first spatial filter (SF1) 711A is arranged in the optical path of reflected light from the illumination area of the microfluidic device 101 to receive the scattered light (e.g., fluorescence emission and backscattering light) from the sample and to temporally and/or spatially encode the received light based on the pattern of openings of the spatial filter 711A. In some implementations, for example, the optical system of the system 700 can include an objective lens 117 configured in the optical path to receive the reflected light from the illumination area of the microfluidic device 101 to focus the reflected light onto the spatial filter 711A. For example, the mask design for the spatial filter (SF1) 711A is positioned at the image plane in the detection path. In this example, the spatial filter 711A includes three groups of slits, e.g., three duplicates of four 100 μm by 1 mm slits positioned apart in a manner where one slit is immediately after another in both x and y-direction. The encoded light is passed from the spatial filter 711A to a resonant scanner (RS) 719 of the optical system, which can be configured to scan vertically (e.g., at 10 kHz). The spatially-encoded light is provided from the RS 719 to the second spatial filter (SF2) 711B to encode a frequency of the optical signal. The example spatial filter (SF2) 711B is shown in FIG. 7 to have three parallel arrays of slit with three different periods, e.g., where one group has 40 periods, one group has 80 periods, and the other has 120 periods. The two spatial filters 711A and 711B are aligned in the optical path of the optical system so that the three slit-groups of one filter are projected to the three slit-groups of the other correspondingly. The optical system is configured to include the second DM 112A, which receives the encoded light from the second spatial filter (SF2) 711B and directs the encoded light to a PMT 114 (or multiple individual PMTs), in electrical communication with the electronic system 120. In the example embodiment shown in FIG. 7, when the PMT 115 collects the light passing through such the optical system, the resultant light intensity signal in this example is the superposition of three signals modulated at 400 kHz, 800 kHz, and 1.2 MHz. The electronic system 120 is configured to process the data signal provided by the PMT 114. For example, after applying Fourier transform to the resulting signal, the light intensity profile of every four rows can be retrieved by band-pass filtering the signal with knowing the carrier frequency, then one can use the disclosed data processing algorithm to obtain every row of the cell image. In implementations of the optical system using fluorescent light signals, for example, the optical system of the imaging flow cytometry system 700 can include the emission filter 113 and the lens 115 in the optical path to filter and focus the encoded fluorescent light into the PMT 114.

Multi-Channel Photodetector Arrays.

In some implementations of the disclosed technology, the disclosed imaging flow cytometer systems can employ a multi-anode PMT as the optical detector in the optical system. The multi-anode PMT is equivalent to incorporating multiple PMTs in a single housing. Since the conventional PMT is a zero-dimensional detector, in which the spatial information of the intensity is lost and summed by one large anode that intercepts all the secondary electrons, multi-anode PMT provides one-dimensional information—the spatial information of intensity along x or y-direction. By using multi-anode PMT instead of single channel PMT, the resolution of the constructed cell image can be instantly increased multiple times according to the number of channels that the multi-anode PMT has. Employing such a photodetector is compatible with any of the three spatial filter design discussed above to provide higher image resolution and/or higher system throughput.

Demonstration of Cell Images with 2-Fluorescent Colors.

Figure 8:
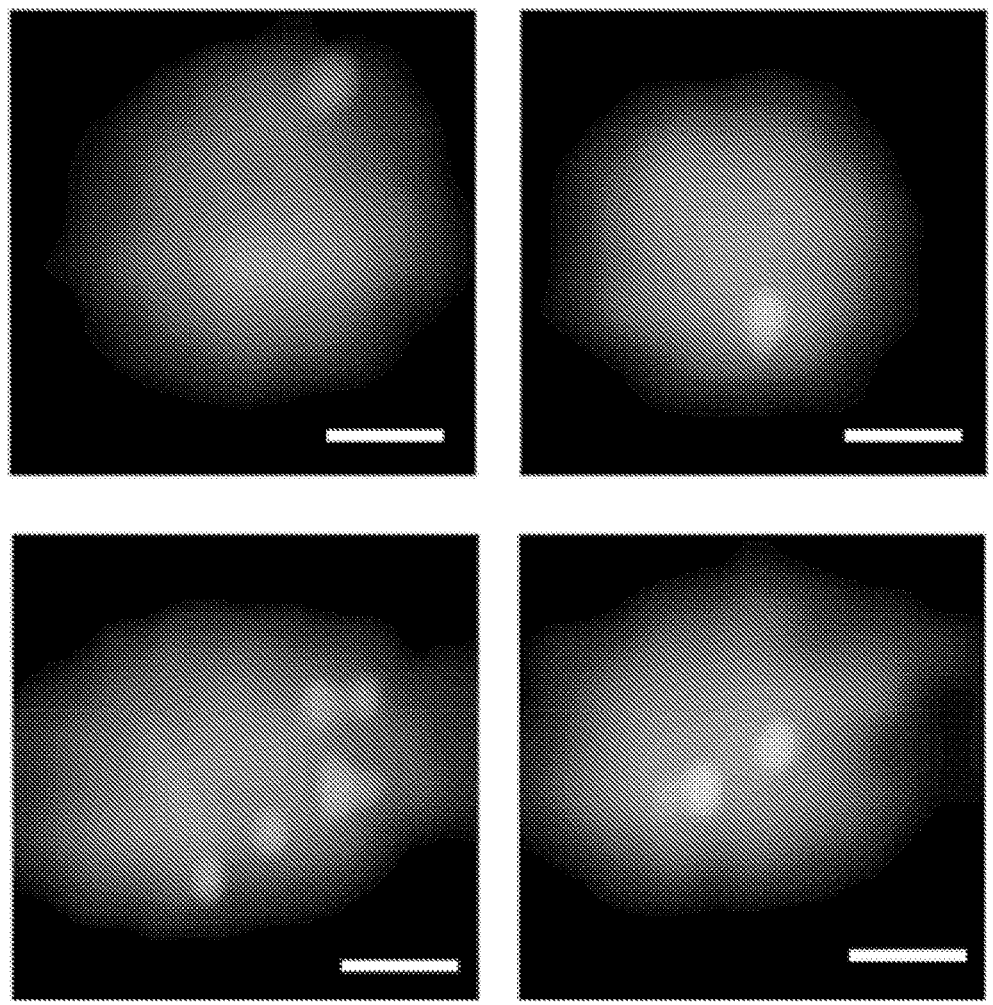
FIG. 8 shows images of exemplary data featuring multi-color cell imaging in flow cytometry implemented by an exemplary imaging flow cytometry system.

Exemplary implementations of the present imaging flow cytometry technology were performed to demonstrate multicolor cell imaging in flow cytometry applications. In the exemplary implementations, MDA-MB-231 human breast cancer cells were stained with CellTrace CFSE (e.g., 520 nm emission), and the cells were labeled with 1 μm carboxylated-modified fluorescent beads (e.g., 630 nm emission) to obtain the images using an exemplary imaging flow cytometer system of the disclosed technology. FIG. 8 shows two-color cell images using the disclosed imaging flow cytometry techniques. The example scale bars in the images of FIG. 8 are 5 μm. The images demonstrate 1.0 to 1.5 μm spatial resolution, in which the image features multi-colored internal features of the particles and their spatial distribution in the cell.

Disclosed is a spatial-temporal transformation technique that enables traditional flow cytometers to capture fluorescence and backscattering images of cells travelling at high speed in fluid stream. The image quality of the disclosed technology is comparable to that of conventional fluorescence microscopy imaging for still cells using a CCD or CMOS camera. The spatially distributed backscattering plots generated by the disclosed system reveal not only the commonality of cells of the same type but also the inhomogeneity of them, exemplified by the same cell type undergoing different life cycles. Because of the simplicity of the design and the use of PMTs (e.g., rather than CCDs) for construction of cell image, the disclosed approaches can convert or retrofit existing flow cytometers into systems with single cell imaging capabilities. While in the exemplary devices and systems used in exemplary implementations show imaging results for two parameters (e.g., one-color fluorescence and backscattering), the disclosed techniques can be applied to produce cell images of multiple fluorescent colors with additional dichroic mirrors and PMTs. Furthermore, the disclosed technology can work at higher fluid flow rate for higher spatial resolution and throughput with high-speed digital data acquisition electronics.

Exemplary Materials and Methods for Some Example Implementations

Microfluidic Device Fabrication.

The exemplary microfluidic devices used in the exemplary implementations was fabricated using polydimethylsiloxane (PDMS) replica molding methods. The Si mold masters were fabricated by the reactive ion etching (RIE) process. The microfluidic channels were drawn in AutoCAD (Autodesk, Inc.), and were photolithographically defined using negative photoresist (NR9-1500PY, Futurrex, Inc.), which serves as an etch mask during the following dry-etching process. A 4-inch silicon wafer was etched at room temperature using inductively coupled plasma (ICP) reactive ion etching (ICP RIE; Plasmalab 100, Oxford Instruments) to reach a depth of 75 µm. Plasma ignited from a mixture of O2 and SF6 gases performed the etching and sidewall passivation, resulting in smooth and vertical channel walls. The Si mold master was silanized by vapor deposition of trichlorosilane (TCI Inc.) to facilitate PDMS de-molding. A replica was made by casting the PDMS (Sylgard 184, Dow Corning), mixed in the standard 10:1 ratio of base to curing agent, over the Si mold master. After thermal curing in the oven for 3 hours at 65° C., the PDMS layer was peeled off of the mold, and holes for inlets and outlets were punched. The surfaces of the demolded PDMS layer and a glass wafer were both treated with UV/Ozone to facilitate covalent bonding of them to form microfluidic channels for the imaging flow cytometer experiment.

Optical System.

The exemplary optical system used in the exemplary implementations used a 25 mW 488-nm single-mode fiber coupled laser (e.g., FTEC2, Blue Sky Research), which has a circular beam shape with Gaussian energy distribution. A top-hat beam shaper (Osela, Inc.) was used to convert the Gaussian beam to a uniform top-hat profile, which illuminates an area of 100 µm (x-direction) by 350 µm (y-direction). The fluorescence passing the miniature dichroic mirror with 500 nm cutoff wavelength (ThorLabs) and the scattering light were collected through a 50×, 0.55NA objective lens (Mituyoyo). The light intensity signal in each channel was acquired by a PMT (H9307-02, Hamamatsu) and recorded using LabVIEW. The saved raw data was processed in MATLAB on a computer, implementing the aforementioned algorithm.

Spatial Filter Fabrication.

The design of spatial filter was drawn in AotoCAD and printed to a transparency mask at 20,000 dots per inch (dpi). A layer of negative photoresist (NR9-1500PY, Futurrex, Inc.) was spun at 3,000 rotations per minute (rpm) on a 6-inch glass wafer. The wafer was heated on a hot plate at 150° C. for 3 minutes then exposed to UV light (EVG620NT, EV Group) through the transparency mask. Post UV exposure, the wafer was baked at 100° C. for another 3 minutes before development in RD6 (Futurrex, Inc.) for 12 seconds. A film of 200 nm thick aluminum was sputtered onto the glass wafer. After metal lift-off, the patterns of the spatial filter were formed and the glass wafer was diced into 15 mm by 15 mm pieces. To help hold the spatial filter in the flow cytometer system, the spatial filter having ten 1 mm by 100 µm slits was mounted to a sample holder fabricated by 3D printing method.

Preparation of Cell Samples.

The A549 human lung adenocarcinoma epithelial cell samples were harvested from culture and labeled with CellTrace CFSE Cell Proliferation Kit (Life technologies) that has excitation and emission peaks at approximately 492 nm and 517 nm, respectively. After incubation in 4% formaldehyde for 20 min, the A549 cells were washed and re-suspended in phosphate buffered saline (PBS). Before every imaging experiment, the suspension was diluted in PBS to a concentration of 200 cells/µL. To arrest A549 cells at the G1 phase, Mitomycin (10 µg/ml) dissolved in DMEM, mixed with 0.5% FBS and 1% PS, was added to the culture medium and then the cells were incubated for 3 hours prior to the experiment. To arrest cells at the G2/M phase, 50 ng/ml of nocodazole in DMEM, mixed with 0.5% FBS and 1% PS, was added to the culture medium and the cells were cultured for 16 hours. Cells arrested at the designed phase were washed with PBS and suspended in 4% formaldehyde. After keeping the cell suspension at room temperature for 20 minutes, the sample was centrifuged at 1000 rpm for 10 min and the supernatant of cell suspension was carefully discarded. After washing the sample left in the tube with PBS, the fixed cells were re-suspended in PBS to the concentration of 200 cells/µL.

Measurements of Cell Morphological Features.

The output images from the imaging flow cytometer represent a 20 µm by 20 µm area; the cell fluorescence images from the fluorescence microscope (BZ-9000, Keyence) were also cropped to the same area. For example, to measure the morphological features of both the cell images restored by the imaging flow cytometer and taken by the fluorescence microscope, all images were processed using ImageJ. Two image sequences that include 100 images from each system were imported to ImageJ. After setting the measurements to include area and shape descriptors, the command "Analyze Particles" was used to measure the concurrently thresholded images. The mean values and the standard deviations in Table 1 were calculated based on the results from ImageJ. For the Feret's diameter measurements of backscattering images, 300 images from each of the G1 arrested cells and the G2/M arrested cells were analyzed using the same method in ImageJ. For example, to avoid multiple measurements in one image due to the disconnected patterns, especially in the backscattering images of G2/M arrested cells, all the images, including both G1 and G2/M cell images, were smoothed twice and concurrently thresholded, and only the largest Feret's diameter in every image was recorded.

Exemplary Applications

Applications of the disclosed technology is envisioned to make conventional and image-based cell-sorting flow cytometry an everyday lab tool by making the exemplary devices and systems disclosed herein portable, affordable, and easy to use. In some implementations, for example, a simple spatial-frequency optical filter of the disclosed technology can be used with flow cytometers (e.g., conventional flow cytometry sensors) to encode image information during flow cytometry applications. In applications directed for emerging markets, like stem cell research, for example, there is a strong need to develop and make available an affordable, user-friendly system that can also generate images for more sophisticated analysis.

Flow cytometry allows for rapid analysis of thousands of cells for qualities such as size (forward scatter), roughness (side-scatter), and the intensity of one or more florescent markers. Image information, however, is difficult to obtain due to the rapid movement of cells through an optical detection zone. Currently, there are some technically sophisticated imaging flow cytometers that exist, but they are much more complex and expensive than conventional flow cytometers and are seldom purchased or used as a result. In addition, no known imaging flow cytometers have the ability to sort cells because of the technical complexity of combining cell sorting with today's imaging flow cytometry. The ability to rapidly characterize cells for conventional flow cytometry properties while collecting image information would enable additional important phenotypic cell characterization to be performed, such as the location of cytosolic vs. nuclear protein expression/localization to advance biomedical discoveries; and such abilities are envisioned to be provided by the imaging flow cytometry systems, devices, and methods of the present technology.

The disclosed technology provides systems, devices, and methods to construct images of a travelling particle (e.g., cell) by passing the fluorescent emission from a cell though a spatial-multiplexed and/or spatial-frequency multiplexed filter before measurement with an optical detector (e.g. photomultiplier tube PMT). For example, PMTs can operate at high frequencies and their output can then be deconvolved with the predetermined spatial and frequency properties of the filter to construct a cell image with adequate (e.g. 2 μm, or less) resolution for most applications. The disclosed techniques can be implemented using only an optical filter as additional hardware to provide any flow cytometer with cell imaging capabilities. The optical spatial and/or spatial-frequency filters of the present technology can be easily manufactured in high volume at low cost, e.g., with photolithographic mask technology; and the disclosed techniques are envisioned to be applied to new flow cytometers or even retrofit existing flow cytometers to obtain substantial performance upgrades. Furthermore, the same principle of the disclosed techniques used to create a fluorescent image of a travelling cell can also be implemented to produce a light scattering (e.g., back scattering) image of unlabeled cells. Using this method, one can image the internal structure (e.g., nucleus) of travelling unlabeled cells for the very first time, a unique and useful capability unavailable for any flow cytometers presently.

Figure 9:
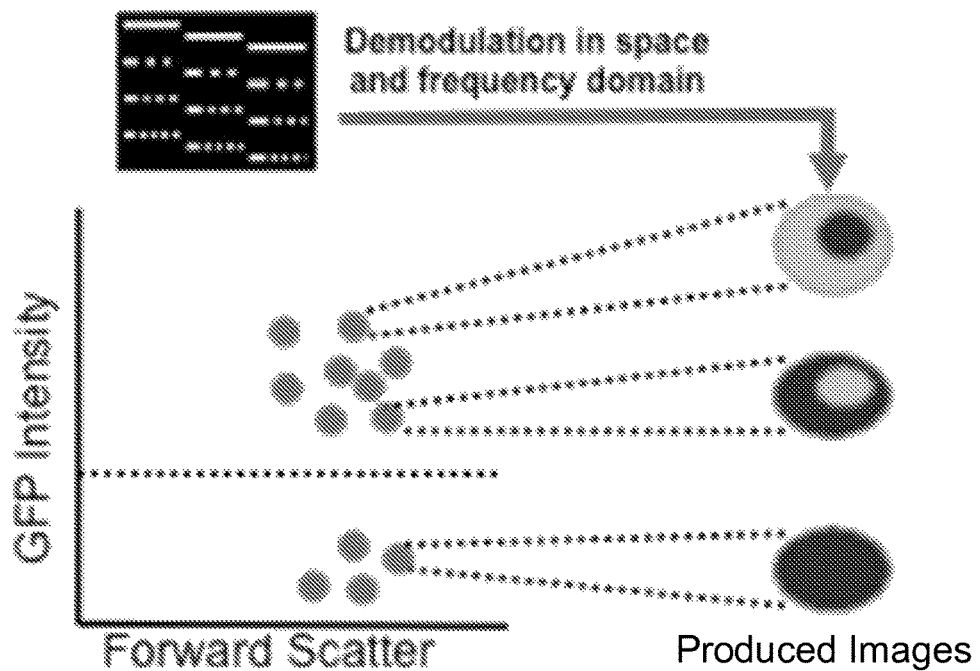
FIG. 9 shows an illustrative diagram of the multi-functional output from the image data produced by the exemplary imaging flow cytometry systems of the present technology.

FIG. 9 shows an illustrative diagram of the multi-functional output from the image data produced by the exemplary imaging flow cytometry systems of the present technology. For example, a conventional flow cytometers lack the ability to define spatial information due to the rapid movement of cells in the detection zone. Also, for example, phenotypic properties of cells can be revealed with conventional microscopy, but does not allow high throughput cell-by-cell analysis or sorting. The diagram of FIG. 9 illustrates the exemplary flow cytometry method to encode image information by using a spatial and/or spatial-frequency filter to create an encoded signal that can be transformed by data processing algorithms to produce image data and render images that distinguish physical characteristics of the particles, e.g., such as cell features like cytoplasmic from nuclear staining. Furthermore, the disclosed technology can be implemented as a microfluidic sorting flow cytometer to enable cells to be imaged and sorted concurrently.

In some implementations, for example, the optical spatial and/or spatial-frequency filter can be placed in front of one or multiple photomultiplier tube (PMT) detectors. The exemplary optical filter can include a matrix of slits with periodic structures (e.g., spatial frequencies) among each column of the slits. The fluorescent or scattering signal from a travelling cell passes this filter before reaching the PMT. The resulting signal from the PMT is then composed of the multiplexed signals modulated by the filter. The time domain and Fourier domain analyses of the PMT signal yield signals of unique temporal and frequency signatures corresponding to the fluorescence generated from different areas of the cell. One can then apply the disclosed mathematical algorithms to decode the signals of different signatures and construct the fluorescence image of the entire cell. For example, for a cell labeled with different fluorophores, the fluorescent image of each color can be superimposed to create the fluorescent image. Also, for example, for unlabeled cells, one can obtain its internal (e.g. nuclear) structure image from the scattering (e.g., back-scattering) signals for WBC classification or cell cycle detection. The resulting image appears to be similar to the image of a static cell observed with a fluorescent microscope, even though in the flow cytometer the cell actually travels at a speed of several meters per second and the image is detected by only a few PMTs (one color for each PMT) instead of a pixelated, high speed imager. The disclosed technology is envisioned to provide a major breakthrough that can potentially revolutionize the field of flow cytometry, and its impact and ramifications on both fundamental biomedical research and clinic applications can be tremendous.

Figure 10:
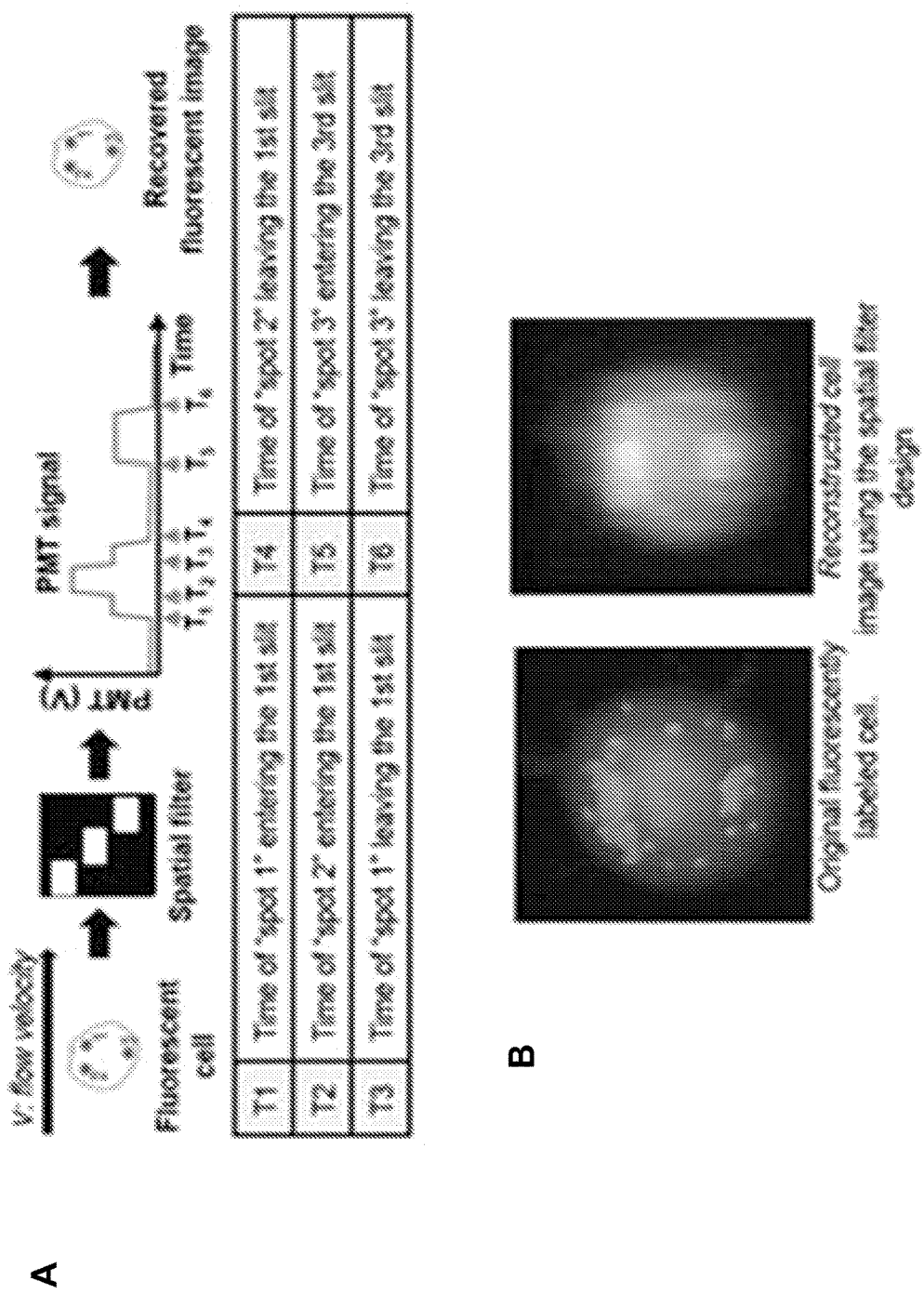
FIG. 10 shows diagrams and images presenting the design and output of an example imaging flow cytometer of the present technology by applying a spatial filter to a conventional flow cytometer.

FIG. 10 includes diagrams and images presenting the design and principle of an example imaging flow cytometer of the present technology by applying a spatial filter to a conventional flow cytometer. For illustration purposes, it is assumed that the cell travelling in the flow chamber at a speed "v" has three discrete spots of fluorescence, as shown in FIG. 10. For example, the optical design of any flow cytometers can be considered as a focusing system that projects the fluorescent emission (after dichroic mirrors and other optical components) onto the photomultiplier tube (PMT). Here, a spatial filter can be placed, as illustrated in panel A of FIG. 10, at the image plane in front of the PMT. Then the fluorescent image of the cell is formed on the plane of the spatial filter with a magnification factor determined by the optics (e.g., a magnification factor of 50×). As the cell travels in the channel at a velocity "v", the image projected onto the spatial filter travels at an effective speed of Mv, where M is the magnification factor. For example, the spatial filter is designed in such a manner that different parts of the cell will pass different slits at different times (e.g., an upper part first, then the middle portion, and finally the bottom part with respect to the example spatial filter shown in FIG. 10). As a result, the waveform of the fluorescent signal from the PMT includes a sequence of patterns separated in time domain, with each section of the signal related to the fluorescence of the corresponding regime of the cell. The table shown in FIG. 10 also shows how the intensity profile in this particular example is related to the characteristic times in the waveform. In the more general case, for example, the fluorescent intensity profile corresponding to each slit can be obtained by taking the time derivative of the waveform. For example, the schematic illustration in panel A of FIG. 10 illustrates using the exemplary spatial filter of the disclosed technology and a PMT, e.g., which can be found in conventional flow cytometers, to reconstruct the fluorescent image of a travelling cell. At left of the panel A, a cell enters the detection zone where it is illuminated by laser light and emits fluorescence. The emitted light passes through a patterned filter and produces a corresponding change in voltage over time from the PMT. Because the pattern of the filter is known, as specific features of the cell pass by the filter and produce PMT voltage changes, a data processing unit implements the image data processing method (e.g., employing an algorithm based on the filter properties) to produce image data, and in some implementations to reconstruct the image. The panel A of FIG. 10 also shows images including an original fluorescently labeled cell (left) and a reconstructed cell image (right) using the data processing method of the disclosed technology based on the exemplary spatial filter design.

For example, spatial filter image reconstruction can be performed based on the following example. After the fluorescent profile over each slit area is recovered, the fluorescent image of the entire cell can be constructed by splicing all the profiles together. The spatial resolution of the restored image depends on the number of slits, the width of each slit, and/or the optics, for example. A spatial resolution in the singular microns (e.g., 2 µm, or less) can be achieved, which is suitable for most applications. It is noted that in some implementations based on factors of the flow cytometer system, the spatial filter design may limit the device throughput and sensitivity because the overall length of the filter in the direction of cell flow requires operation at a reduced sample density to keep the frequency of coincidence events low. A co-incident event occurs when the second cell enters the filter area before the first cell leaves the area. The extended excitation area corresponding to the long filter may also reduce the fluorescent intensity and affects the sensitivity of the system, in some implementations. Therefore, the spatial filter design can include a spatial-frequency filter.

Figure 11:
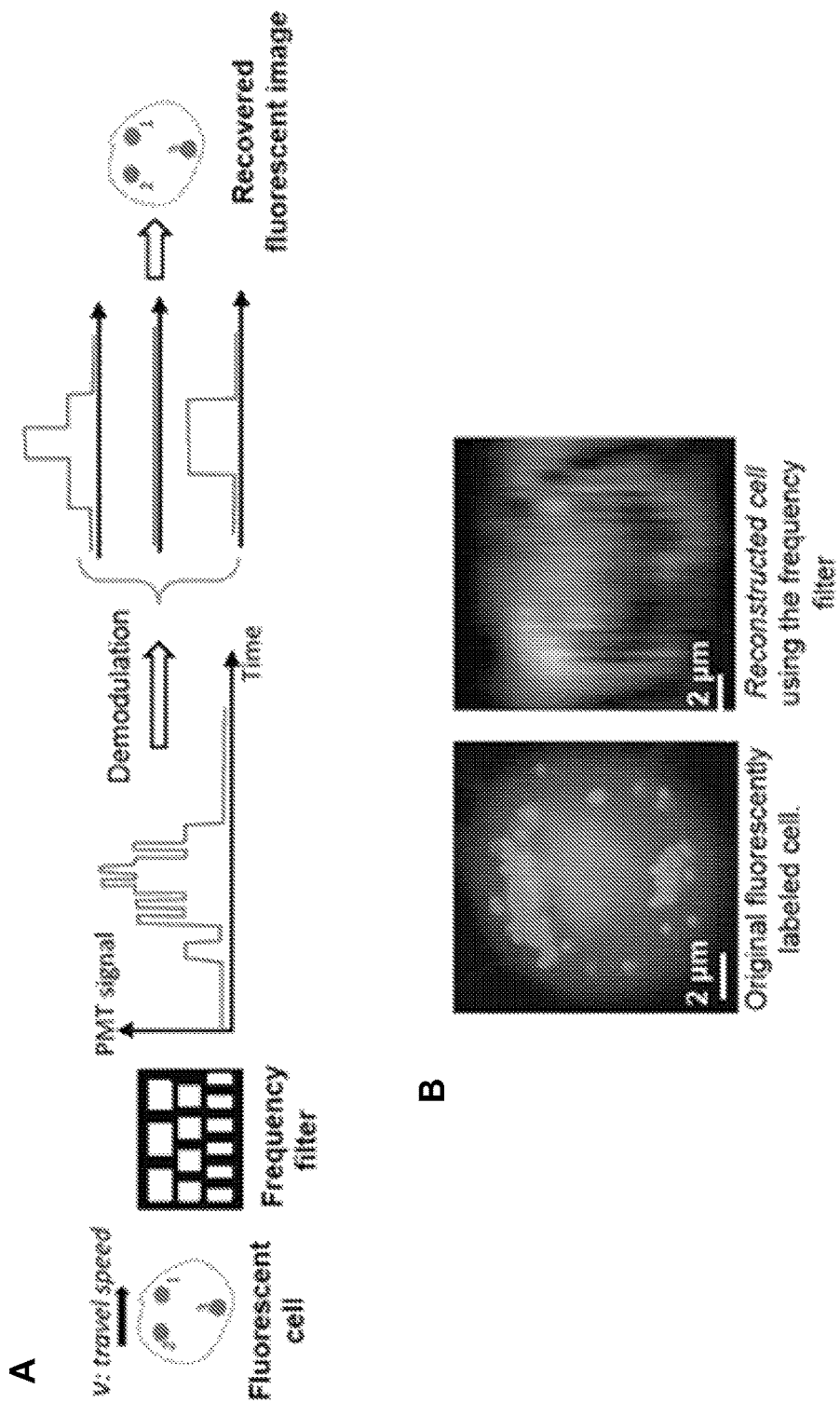
FIG. 11 shows diagrams and images presenting the design and output of an example imaging flow cytometer of the present technology using a spatial frequency filter to restore the cell fluorescent image.

FIG. 11, panel A, shows another example design of using a spatial frequency filter to restore the cell fluorescent image. The spatial-frequency filter includes a parallel array of slits, and each slit has a periodic structure with a unique value periodicity. When a cell travels through the filter regime, the fluorescent profile is displayed as a convoluted amplitude modulated signal riding on a characteristic carrier frequency. In this manner, the signal produced by each fluorescent regime of the cell is encoded by a specific carrier frequency. After demodulation, the fluorescent intensity profile of the cell can be obtained. Panel B of FIG. 11 shows a cell image recovered from the signal after the frequency filter where 10 carrier frequencies have been used to slice the cell into 10 rows. It is noted, for example, that although the image quality is limited by the crosstalk among different frequency components and the bandwidth of the detector, localized fluorescent features within a cell can be resolved.

Figure 12:
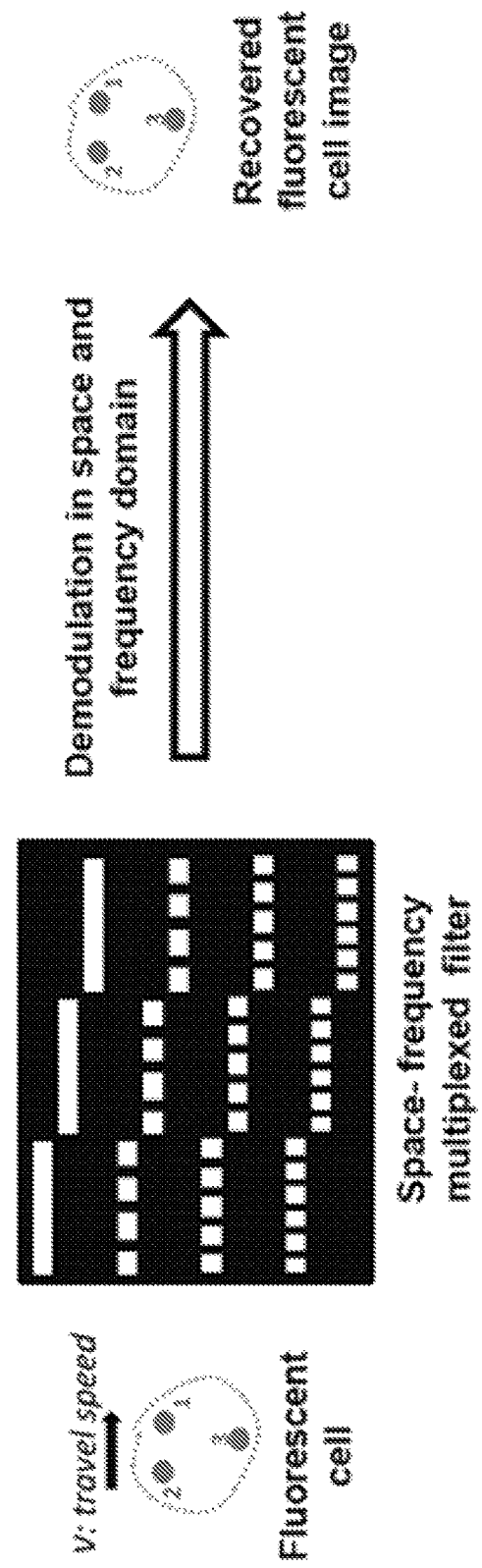
FIG. 12 shows an exemplary design of a multiplexed spatial-frequency filter that can be incorporated into conventional flow cytometers with maximum compatibility.

FIG. 12 shows an exemplary design of a multiplexed spatial-frequency filter that can be incorporated into conventional flow cytometers with maximum compatibility. The example filter design shown in FIG. 12 includes three columns of slits and each column of the slits has four periodic structures that define four carrier frequencies (including the baseband defined by the open slit). In this example of FIG. 12, the detected PMT waveform is equivalent to the superposition of the waveforms in FIGS. 10 and 11. For example, after demodulation in time and frequency domains, one can obtain the fluorescent profile of the entire cell. Compared to the pure spatial filter approach, the length of the filter required to achieve the same image resolution is reduced by 4×. As a result, the length of the laser excitation area and the fluorescence collection area is reduced from 240 µm to 60 µm. This is compatible with the optical design of conventional flow cytometers (e.g., having a beam spot of 60 µm by 20 µm, with 60 µm along the flow direction). For example, only three different frequencies were used (without including the baseband (e.g., zero frequency)), and therefore the sampling rate and bandwidth of the PMT are greatly reduced compared to the frequency filter design.

Examples

The following examples are illustrative of several embodiments of the present technology. Other exemplary embodiments of the present technology may be presented prior to the following listed examples, or after the following listed examples.

In an example of the present technology (example 1), a method for imaging particles in flow cytometry includes transmitting a light beam at a fluidic channel carrying a fluid sample containing particles, such that the light beam is scattered by the particles or causes fluorescent emission from the particles in the fluidic channel; receiving the scattered or fluorescently-emitted light at a spatial optical filter, the spatial optical filter including a surface having a plurality of apertures arranged in a pattern along a transverse direction opposite to particle flow and a longitudinal direction parallel to particle flow, such that different portions of a particle flowing over the pattern of the apertures pass different apertures at different times and scatter the light beam or emit fluorescent light at locations associated with the apertures; encoding an optical signal including spatial and temporal information of the particle based on at least some of the received scattered or emitted fluorescent light from the fluidic channel carrying the fluid sample; detecting the encoded optical signal by an optical detector; and processing the detected optical signal, at a data processing unit in communication with the optical detector, to produce image data associated with the particle flowing through the fluidic channel, in which the produced image data includes information of a physical characteristic of the particle.

Example 2 includes the method of example 1, further including forming an image of the particle based on the produced image data, in which the image includes a visual presentation of the physical characteristic of the particle.

Example 3 includes the method of example 1, in which the processing the detected optical signal is in real-time as the particles flow in the fluidic channel.

Example 4 includes the method of example 1, in which the processing the detected optical signal includes: determining a position or a velocity of the particle in at least two dimensions; determining a characteristic function of the spatial optical filter, the characteristic function including parameters associated with size and arrangement of the apertures in the pattern; and determining a localized signal associated with one or more portions of the particle to produce the image data associated with the particle by deconvolving a particle signal with the determined characteristic function, in which the particle signal includes the detected optical signal, the determined position or velocity, a magnification of an optical system to focus the received scattered or fluorescently-emitted light at the spatial optical filter.

Example 5 includes the method of example 1, further including sorting the particles based on the determined physical characteristic of the particles.

Example 6 includes the method of example 1, in which the physical characteristic of the particles in the produced image data includes at least one of a size of the particle, a spatial feature or geometry of the particle, or a location or concentration of an internal feature of the particle.

Example 7 includes the method of examples 1 or 6, in which the particles include biological cells.

Example 8 includes the method of example 7, in which the produced image data includes spatial distribution data of fluorescence patterns of internal organelles, the nucleus, or a parasitic substance in the biological cell.

Example 9 includes the method of example 1, in which the produced image data includes scattering pattern data of the particle due to shape and density distribution of the particle.

Example 10 includes the method of example 1, in which the pattern of apertures includes two or more slits positioned apart such that an adjacent slit is positioned outside a coverage area of a slit with respect to both the longitudinal direction of particle flow in the fluidic channel (y-direction) and the transverse direction perpendicular to the longitudinal direction (x-direction).

Example 11 includes the method of example 10, in which the pattern of apertures includes ten 100 μm by 1 mm slits.

Example 12 includes the method of example 1, in which the pattern of apertures includes groups of slits, in which each group of slits includes two or more parallel arrays of slits that are shifted and spatially isolated and non-overlapping in the longitudinal direction of particle flow in the fluidic channel (y-direction).

Example 13 includes the method of example 1, further including encoding frequency information in the optical signal by a second optical filter positioned in the optical path and an imaging plane of the optical detector, the second optical filter including a pattern of frequency modulating apertures including two or more groups of slits having parallel arrays of slits at a spacing to create different periods with respect to the groups.

Example 14 includes the method of example 1, in which the light beam includes a laser beam.

Example 15 includes the method of example 1, in which the optical detector includes one or more photomultiplier tubes (PMT).

In an example of the present technology (example 16), an imaging flow cytometer system includes a fluidic device structured to include a substrate and a fluidic channel disposed on the substrate to carry a fluid sample containing particles along a particle flow direction; a light source to generate a light beam at the fluidic channel to illuminate the fluid sample, in which, when illuminated by the light beam, light is scattered by the particles or causes fluorescent emission from the particles; an optical detector arranged in an optical path of the scattered or fluorescently-emitted light; an optical filter positioned in an imaging plane of the optical detector and structured to include a surface having a plurality of apertures arranged in a pattern along a transverse direction opposite to and a longitudinal direction parallel to the particle flow direction, such that different portions of a particle flowing over the pattern of the apertures pass different apertures at different times and scatter the light beam or emit fluorescent light at locations associated with the apertures, in which the optical filter is operable to encode an optical signal including spatial and temporal information of the particle based on at least some of the received scattered or emitted fluorescent light from the fluidic channel carrying the fluid sample, such that the encoded optical signal is detected by the optical detector; and a data processing unit in communication with the optical detector, the data processing unit to process the encoded optical signal to produce image data associated with the particle flowing through the fluidic channel, in which the produced image data includes information of a physical characteristic of the particle.

Example 17 includes the system of example 16, in which the data processing unit is configured to process the produced image data to generate an image of the particle, in which the image includes a visual presentation of the physical characteristic of the particle.

Example 18 includes the system of example 16, in the data processing unit is configured to process the encoded optical signal to produce the image data by determining a position or a velocity of the particle in at least two dimensions; determining a characteristic function of the optical filter, the characteristic function including parameters associated with size and arrangement of the apertures in the pattern; and determining a localized signal associated with one or more portions of the particle to produce the image data associated with the particle by deconvolving a particle signal with the determined characteristic function, in which the particle signal includes the detected optical signal, the determined position or velocity, a magnification of an optical system to focus the received scattered or fluorescently-emitted light at the optical filter.

Example 19 includes the system of example 16, in which the system is operable to sort the particles based on the determined physical characteristic of the particles, in which the fluidic device includes an actuator at a second region of the fluidic channel after a first region of the fluidic channel where the light beam is illuminated, the actuator in communication with the data processing unit to receive a command to sort the particles according to the determined physical characteristic.

Example 20 includes the system of example 16, in which the physical characteristic of the particles in the produced image data includes at least one of a size of the particle, a spatial feature or geometry of the particle, or a location or concentration of an internal feature of the particle.

Example 21 includes the system of examples 16 or 20, in which the particles include biological cells.

Example 22 includes the system of example 21, in which the internal feature of the biological cell includes a cell organelle or a non-native substance of the cell.

Example 23 includes the system of example 16, in which the data processing unit includes an input/output unit operable to interface with an external computer system to provide the produced image data to and receive data from the external computer system.

Example 24 includes the system of example 16, in which the data processing unit is resident on an external computer system.

Example 25 includes the system of example 24, in which the external computer system includes a personal computer, a tablet, a smartphone, or a wearable communication device.

Example 26 includes the system of example 16, in which the pattern of apertures of the optical filter includes two or more slits positioned apart such that an adjacent slit is positioned outside a coverage area of a slit with respect to both the longitudinal direction of particle flow in the fluidic channel (y-direction) and the transverse direction perpendicular to the longitudinal direction (x-direction).

Example 27 includes the system of example 26, in which the pattern of apertures includes ten 100 μm by 1 mm slits.

Example 28 includes the system of example 16, in which the pattern of apertures of the optical filter includes groups of slits, in which each group of slits includes two or more parallel arrays of slits that are shifted and spatially isolated and non-overlapping in the longitudinal direction of particle flow in the fluidic channel (y-direction).

Example 29 includes the system of example 16, further including a second optical filter positioned in the optical path and an imaging plane of the optical detector, the second optical filter including a pattern of frequency modulating apertures including two or more groups of slits having parallel arrays of slits at a spacing to create different periods with respect to the groups.

Example 30 includes the system of example 16, in which the light source includes a laser, and the light beam includes a laser beam.

Example 31 includes the system of example 16, in which the optical detector includes one or more photomultiplier tubes (PMT).

In an example of the present technology (example 32), an optical spatial filter for encoding an optical signal from particles flowing in a fluidic channel includes a substrate having a plurality of apertures arranged in a pattern along a transverse direction opposite to and a longitudinal direction parallel to a particle flow direction of the particles flowing in the fluidic channel, in which the optical spatial filter is operable to encode the optical signal from the particle flowing in the fluidic channel when positioned in an optical path between an illumination region of the fluidic channel upon which a light beam illuminates and an optical detector, in which the optical spatial filter is positioned in an imaging plane of the optical detector, in which the optical spatial filter is operable to encode the optical signal based on different portions of a particle flowing over the pattern of the apertures pass different apertures at different times and scatter the light beam or emit fluorescent light at locations associated with the apertures, in which the encoded optical signal includes spatial and temporal information of the particle based on at least some of the received scattered or emitted fluorescent light from the fluidic channel.

Example 33 includes the optical spatial filter of example 32, in which the spatial and temporal information of the optical signal encoded by the optical spatial filter provides data including a physical characteristic of the particle that is able to be processed to produce image data associated with the particle flowing through the fluidic channel, in which the image data is producible by determining a position or a velocity of the particle in at least two dimensions; determining a characteristic function of the optical spatial filter, the characteristic function including parameters associated with size and arrangement of the apertures in the pattern; and determining a localized signal associated with one or more portions of the particle to produce the image data associated with the particle by deconvolving a particle signal with the determined characteristic function, in which the particle signal includes the detected optical signal, the determined position or velocity, a magnification of an optical system to focus the received scattered or fluorescently-emitted light at the spatial optical filter.

Example 34 includes the optical spatial filter of example 32, in which the pattern of apertures includes two or more slits positioned apart such that an adjacent slit is positioned outside a coverage area of a slit with respect to both the longitudinal direction of particle flow in the fluidic channel (y-direction) and the transverse direction perpendicular to the longitudinal direction (x-direction).

Example 35 includes the optical spatial filter of example 34, in which the pattern of apertures includes ten 100 μm by 1 mm slits.

Example 36 includes the optical spatial filter of example 32, in which the pattern of apertures of the optical filter includes two or more groups of slits, in which each group of slits includes two or more parallel arrays of slits that are shifted and spatially isolated and non-overlapping in the longitudinal direction of particle flow in the fluidic channel (y-direction).

Example 37 includes the optical spatial filter of example 36, in which the optical spatial filter further includes a second optical filter positioned in the optical path and an imaging plane of the optical detector, the second optical filter including a pattern of frequency modulating apertures including two or more groups of slits having parallel arrays of slits at a spacing to create different periods with respect to the groups.

Example 38 includes the optical spatial filter of example 37, in which the second optical filter includes three groups, where the slits of the first group are spaced at a first period, the slits of the second group are spaced at a multiple of the first period, and the slits of the third group are spaced at a multiple of the first or the second periods.

In an example of the present technology (example P1), a method of imaging a particle in a flow cytometer includes transmitting a light beam through a pattern of apertures spatially arranged about a fluidic channel to illuminate a fluid sample containing particles, in which the pattern of apertures includes a substrate structured to form a plurality of slits arranged on the substrate such that different portions of a particle flowing across the pattern of apertures will pass different slits at different times and scatter the light beam to produce optical scattering signals; detecting at least some of the optical scattering signals by an optical detector; and encoding a waveform including spatial and temporal information of the particles based on the optical scattering signals.

Example P2 includes the method of example P1, in which the pattern of apertures includes two or more slits positioned apart such that an adjacent slit is positioned outside a coverage area of a slit with respect to both a longitudinal direction of particle flow in the fluidic channel (y-direction) and a transverse direction perpendicular to the longitudinal direction (x-direction).

Example P3 includes the method of example P3, in which the pattern of apertures includes ten 100 μm by 1 mm slits.

Example P4 includes the method of example P1, in which the pattern of apertures includes groups of slits, in which each group of slits includes three parallel arrays of slits that are shifted and spatially isolated and non-overlapping in a longitudinal direction of particle flow in the fluidic channel (y-direction).

Example P5 includes the method of example P1, in which the light beam includes a laser beam.

Example P6 includes the method of example P1, in which the optical detector includes one or more photomultiplier tubes (PMT).

Example P2 includes the method of example P1, further including processing the encoded waveform to determine a physical characteristic of the particle; and forming an image of the particle including the physical characteristic.

Example P7 includes the method of example P1, in which the particles include cells.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the embodiments and implementations described in the specification, together with the drawings, be considered exemplary, where exemplary means an example. As used herein, the singular forms "a", "an" and "the" are intended to include the plural forms as well, unless the context clearly indicates otherwise. Additionally, the use of "or" may include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for imaging particles in flow cytometry, comprising:

transmitting a light beam at a fluidic channel carrying a fluid sample containing particles, such that the light beam is scattered by the particles or causes fluorescent emission from the particles in the fluidic channel;

receiving the scattered or fluorescently-emitted light at a spatial optical filter, the spatial optical filter including a surface having a plurality of apertures arranged in a pattern along a transverse direction opposite to particle flow and a longitudinal direction parallel to particle flow, such that different portions of a particle flowing over the pattern of the apertures pass different apertures at different times and scatter the light beam or emit fluorescent light at locations associated with the apertures;

encoding an optical signal including spatial and temporal information of the particle based on at least some of the received scattered or emitted fluorescent light from the fluidic channel carrying the fluid sample;

detecting the encoded optical signal by an optical detector; and processing the detected optical signal, at a data processing unit in communication with the optical detector, to produce image data associated with the particle flowing through the fluidic channel, wherein the produced image data includes information of a physical characteristic of the particle.

2. The method of claim 1, further comprising:

forming an image of the particle based on the produced image data, wherein the image includes a visual presentation of the physical characteristic of the particle.

3. The method of claim 1, wherein the processing the detected optical signal is in real-time as the particles flow in the fluidic channel.

4. The method of claim 1, wherein the processing the detected optical signal includes:

determining a position or a velocity of the particle in at least two dimensions;

determining a characteristic function of the spatial optical filter, the characteristic function including parameters associated with size and arrangement of the apertures in the pattern; and determining a localized signal associated with one or more portions of the particle to produce the image data associated with the particle by deconvolving a particle signal with the determined characteristic function, wherein the particle signal includes the detected optical signal, the determined position or velocity, a magnification of an optical system to focus the received scattered or fluorescently-emitted light at the spatial optical filter.

5. The method of claim 1, further comprising:
sorting the particles based on the determined physical characteristic of the particles.

6. The method of claim 1, wherein the physical characteristic of the particles in the produced image data includes at least one of a size of the particle, a spatial feature or geometry of the particle, or a location or concentration of an internal feature of the particle.

7. The method of claim 1, wherein the particles include biological cells.

8. The method of claim 7, wherein the produced image data includes spatial distribution data of fluorescence patterns of internal organelles, the nucleus, or a parasitic substance in the biological cell.

9. The method of claim 1, wherein the produced image data includes scattering pattern data of the particle due to shape and density distribution of the particle.

10. The method of claim 1, wherein the pattern of apertures includes two or more slits positioned apart such that an adjacent slit is positioned outside a coverage area of a slit with respect to both the longitudinal direction of particle flow in the fluidic channel (y-direction) and the transverse direction perpendicular to the longitudinal direction (x-direction).

11. The method of claim 1, wherein the pattern of apertures includes groups of slits, in which each group of slits includes two or more parallel arrays of slits that are shifted and spatially isolated and non-overlapping in the longitudinal direction of particle flow in the fluidic channel (y-direction).

12. The method of claim 1, further comprising:
encoding frequency information in the optical signal by a second optical filter positioned in the optical path and an imaging plane of the optical detector, the second optical filter including a pattern of frequency modulating apertures including two or more groups of slits having parallel arrays of slits at a spacing to create different periods with respect to the groups.

13. The method of claim 1, wherein the optical detector includes one or more photomultiplier tubes (PMT).

14. An imaging flow cytometer system, comprising:
a fluidic device structured to include a substrate and a fluidic channel disposed on the substrate to carry a fluid sample containing particles along a particle flow direction;
a light source to generate a light beam at the fluidic channel to illuminate the fluid sample, wherein, when illuminated by the light beam, light is scattered by the particles or causes fluorescent emission from the particles;
an optical detector arranged in an optical path of the scattered or fluorescently-emitted light;
an optical filter positioned in an imaging plane of the optical detector and structured to include a surface having a plurality of apertures arranged in a pattern along a transverse direction opposite to and a longitudinal direction parallel to the particle flow direction, such that different portions of a particle flowing over the pattern of the apertures pass different apertures at different times and scatter the light beam or emit fluorescent light at locations associated with the apertures, wherein the optical filter is operable to encode an optical signal including spatial and temporal information of the particle based on at least some of the received scattered or emitted fluorescent light from the fluidic channel carrying the fluid sample, such that the encoded optical signal is detected by the optical detector; and
a data processing unit in communication with the optical detector, the data processing unit to process the encoded optical signal to produce image data associated with the particle flowing through the fluidic channel, wherein the produced image data includes information of a physical characteristic of the particle.

15. The system of claim 14, wherein the data processing unit is configured to process the produced image data to generate an image of the particle, wherein the image includes a visual presentation of the physical characteristic of the particle.

16. The system of claim 14, in the data processing unit is configured to process the encoded optical signal to produce the image data by determining a position or a velocity of the particle in at least two dimensions; determining a characteristic function of the optical filter, the characteristic function including parameters associated with size and arrangement of the apertures in the pattern; and determining a localized signal associated with one or more portions of the particle to produce the image data associated with the particle by deconvolving a particle signal with the determined characteristic function, wherein the particle signal includes the detected optical signal, the determined position or velocity, a magnification of an optical system to focus the received scattered or fluorescently-emitted light at the optical filter.

17. The system of claim 14, wherein the system is operable to sort the particles based on the determined physical characteristic of the particles, wherein the fluidic device includes an actuator at a second region of the fluidic channel after a first region of the fluidic channel where the light beam is illuminated, the actuator in communication with the data processing unit to receive a command to sort the particles according to the determined physical characteristic.

18. The system of claim 14, wherein the physical characteristic of the particles in the produced image data includes at least one of a size of the particle, a spatial feature or geometry of the particle, or a location or concentration of an internal feature of the particle.

19. The system of claim 14, wherein the particles include biological cells.

20. The system of claim 19, wherein the internal feature of the biological cell includes a cell organelle or a non-native substance of the cell.

21. The system of claim 14, wherein the data processing unit includes an input/output unit operable to interface with an external computer system to provide the produced image data to and receive data from the external computer system.

22. The system of claim 14, wherein the data processing unit is resident on an external computer system including a personal computer, a tablet, a smartphone, or a wearable communication device.

23. The system of claim 14, wherein the pattern of apertures of the optical filter includes two or more slits positioned apart such that an adjacent slit is positioned outside a coverage area of a slit with respect to both the longitudinal direction of particle flow in the fluidic channel (y-direction) and the transverse direction perpendicular to the longitudinal direction (x-direction).

24. The system of claim 14, wherein the pattern of apertures of the optical filter includes groups of slits, in which each group of slits includes two or more parallel arrays of slits that are shifted and spatially isolated and non-overlapping in the longitudinal direction of particle flow in the fluidic channel (y-direction).

25. The system of claim 14, further comprising a second optical filter positioned in the optical path and an imaging plane of the optical detector, the second optical filter including a pattern of frequency modulating apertures including two or more groups of slits having parallel arrays of slits at a spacing to create different periods with respect to the groups.

26. The system of claim 14, wherein the optical detector includes one or more photomultiplier tubes (PMT).

* * * * *